US007189738B2

(12) United States Patent
Straub et al.

(10) Patent No.: US 7,189,738 B2
(45) Date of Patent: *Mar. 13, 2007

(54) SUBSTITUTED ISOINDOLES AND THEIR USE THEREOF

(75) Inventors: Alexander Straub, Wuppertal (DE); Thomas Lampe, Dusseldorf (DE); Jens Pohlmann, Wuppertal (DE); Susanne Rohrig, Essen (DE); Elisabeth Perzborn, Wuppertal (DE); Karl-Heinz Schlemmer, Wuppertal (DE)

(73) Assignee: Bayer Healthcare AG, Leverkusen (DE)

( * ) Notice: Subject to any disclaimer, the term of this patent is extended or adjusted under 35 U.S.C. 154(b) by 4 days.

This patent is subject to a terminal disclaimer.

(21) Appl. No.: 10/485,412

(22) PCT Filed: Jul. 17, 2002

(86) PCT No.: PCT/EP02/07957

§ 371 (c)(1),
(2), (4) Date: Jan. 30, 2004

(87) PCT Pub. No.: WO03/011858

PCT Pub. Date: Feb. 13, 2003

(65) Prior Publication Data

US 2004/0215019 A1 Oct. 28, 2004

(30) Foreign Application Priority Data

Jul. 30, 2001 (DE) ................................ 101 37 163

(51) Int. Cl.
*A61K 31/454* (2006.01)
*A61K 31/4545* (2006.01)
*C07D 211/22* (2006.01)
*C07D 401/14* (2006.01)

(52) U.S. Cl. ...................... 514/318; 514/323; 546/194; 546/201

(58) Field of Classification Search ................ 546/194, 546/201
See application file for complete search history.

(56) References Cited

U.S. PATENT DOCUMENTS 6,140,351 A 10/2000 Arnaiz et al. ............... 514/336
2003/0045552 A1 * 3/2003 Robarge et al. ............. 514/323

FOREIGN PATENT DOCUMENTS

| WO | 9900121 | 1/1999 |
| WO | 9906371 | 2/1999 |
| WO | 9937304 | 7/1999 |
| WO | 0177075 | 10/2001 |
| WO | 0234711 | 5/2002 |

OTHER PUBLICATIONS

Database Chemcats 'Online!, Chemical Abstract Service, Columbus, Ohio, US; retrieved from STN, XP002215164, order No. F0161-0413 & "Interchim Intermediates," Jul. 9, 2002, Interchim, 213 Avenue Kentucky, BP 1140, Montlucon, Cedex 03103, France.*
Japtap, et al., "Preparation of nucleosides and isoindolinone derivatives as anit-inflamatory agents," STN International, HCAPLUS, Documen No. 135:304105 (2005).*
Database Chemcats 'Online!, Chemical Abstracts Service, Columbus, Ohio, US; retrieved from STN, XP002215164, order No. F0161-0413 & "Interchim Intermediates", Jul. 9, 2002, Interchim, 213 Avenue Kennedy, BP 1140, Montlucon, Cedex 03103, France.
Rohrer, et al., "Iron Environment in Ferritin with Large Amounts of Phosphate, from *Azotobacter vinelandii* and Horse Spleen, Analyzed Using Extended X-ray Absorption Fine Structure (EXAFS)", Biochemistry, 29: 259-264 (1990).
Pschyrembel, Klinisches Wörterbuch, 257th Edition 1994, Walter de Gruyter Verlag, pp. 199-200.
Pschyrembel, Klinisches Wörterbuch, 257th Edition 1994, Walter de Gruyter Verlag, pp. 292-293.
Pschyrembel, Klinisches Wörterbuch, 257th Edition 1994, Walter de Gruyter Verlag, pp. 160-161.
Hauptmann, et al., "Synthetic Inhibitors of Thrombin and Factor Xa: From Bench to Bedside", Thrombosis Res., 93: 203-241 (1999).
Al-Obeidi, et al., "Factor Xa inhibitors by classical and combinatorial chemistry", DDT, 3(5): 223-231 (1998).
Al-Obeidi, et al., "Factor Xa inhibitors", Exp. Opin. Ther. Patents, 9(7): 931-953 (1999).

(Continued)

*Primary Examiner*—Joseph K. McKane
*Assistant Examiner*—Andrew B. Freistein

(57) ABSTRACT

The invention relates to coagulation of the blood. Disclosed are novel compounds of formula (I),

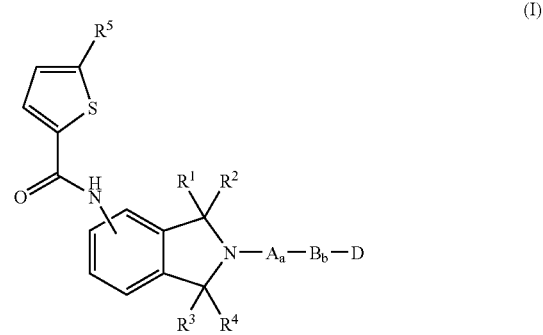

a method for the production of these compounds, pharmaceutical compositions containing them, and methods of using them for the prevention and/or treatment of various diseases.

7 Claims, No Drawings

OTHER PUBLICATIONS

Kaiser, B., "Thrombin and factor Xa inhibitors", Drugs of the Future, 23(4): 423-436 (1998).

Uzan, A., "Antithrombotic agents", Emerging Drugs, 3: 189-208 (1998).

Zhu, et al., "Recent advances in inhibitors of factor Xa in the prothrombinase complex", Curr. Opin. Card. Pulm. Ren. Inv. Drugs, 1(1): 63-87 (1999).

Berry, et al., "Antithrombotic actions of argatroban in rat models of venous, 'mixed' and arterial thrombosis, and its effects on the tail transection bleeding time", Br. J. Pharmacol., 113: 1209-1214 (1994).

Meng, et al., "Effect of Acetylsalicylic Acid on Experimentally Induced Arterial Thrombosis in Rats", Naunyn-Schmiedeberg's Arch. Pharmacol., 301: 115-119 (1977).

* cited by examiner

SUBSTITUTED ISOINDOLES AND THEIR USE THEREOF

The present invention relates to the field of blood coagulation. In particular, the present invention relates to novel isoindole derivatives, to processes for their preparation and to their use as active-compounds in medicaments.

Blood coagulation is a protective mechanism of the organism which helps to "seal" defects in the wall of the blood vessels quickly and reliably. Thus, loss of blood can be avoided or kept to a minimum. Hemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here factor Xa, which is formed from the proenzyme factor X, plays a key role, since it connects the two coagulation paths. The activated serine protease Xa cleaves prothrombin to thrombin. The resulting thrombin, in turn, cleaves fibrinogen to fibrin, a fibrous/gelatinous coagulant. In addition, thrombin is a potent effector of platelet aggregation which likewise contributes significantly to hemostasis.

Maintenance of normal hemostasis—between bleeding and thrombosis—is subject to a complex regulatory mechanism. Uncontrolled activation of the coagulant system or defective inhibition of the activation processes may cause formation of local thrombi or embolisms in vessels (arteries, veins, lymph vessels) or in heart cavities. This may lead to serious disorders, such as myocardial infarct, angina pectoris (including unstable angina), reocclusions and restenoses after angioplasty or aortocoronary bypass, stroke, transitory ischemic attacks, peripheral arterial occlusive disorders, pulmonary embolisms or deep venous thromboses; hereinbelow, these disorders are collectively also referred to as thromboembolic disorders. In addition, in the case of consumption coagulopathy, hypercoagulability may—systemically—result in disseminated intravascular coagulation.

These thromboembolic disorders are the most frequent cause of morbidity and mortality in most industrialized countries (Pschyrembel, Klinisches Wörterbuch [clinical dictionary], 257th edition, 1994, Walter de Gruyter Verlag, page 199 ff., entry "Blutgerinnung" [blood coagulation]; Römpp Lexikon Chemie, Version 1.5, 1998, Georg Thieme Verlag Stuttgart, entry "Blutgerinnung"; Lubert Stryer, Biochemie [biochemistry], Spektrum der Wissenschaft Verlagsgesellschaft mbH Heidelberg, 1990, page 259 ff.).

The anticoagulants, i.e. substances for inhibiting or preventing blood coagulation, which are known from the prior art have various, often grave disadvantages. Accordingly, in practice, an efficient treatment method or prophylaxis of thromboembolic disorders is very difficult and unsatisfactory.

In the therapy and prophylaxis of thromboembolic disorders, use is firstly made of heparin, which is administered parenterally or subcutaneously. Owing to more favorable pharmacokinetic properties, preference is nowadays more and more given to low-molecular-weight heparin; however, even with low-molecular-weight heparin, it is not possible to avoid the known disadvantages described below, which are involved in heparin therapy. Thus, heparin is ineffective when administered orally and has a relatively short half-life. Since heparin inhibits a plurality of factors of the blood coagulation cascade at the same time, the action is nonselective. Moreover, there is a high risk of bleeding; in particular, brain hemorrhages and gastrointestinal bleeding may occur, which may result in thrombopenia, drug-induced alopecia or osteoporosis (Pschyrembel, Klinisches Wörterbuch, 257th edition, 1994, Walter de Gruyter Verlag, page 610, entry "Heparin"; Römpp Lexikon Chemie, Version 1.5, 1998, Georg Thieme Verlag Stuttgart, entry "Heparin").

A second class of anticoagulants are the vitamin K antagonists. These include, for example, 1,3-indanediones, and especially compounds such as warfarin, phenprocoumon, dicumarol and other coumarin derivatives which inhibit the synthesis of various products of certain vitamin K-dependent coagulation factors in the liver in a nonselective manner. Owing to the mechanism of action, however, the onset of the action is very slow (latency to the onset of action 36 to 48 hours). It is possible to administer the compounds orally; however, owing to the high risk of bleeding and the narrow therapeutic index, a time-consuming individual adjustment and monitoring of the patient are required. Moreover, other adverse effects, such as gastrointestinal disturbances, hair loss and skin necroses, have been described (Pschyrembel, Klinisches Wörterbuch, 257th edition, 1994, Walter de Gruyter Verlag, page 292 ff., entry "coumarin derivatives"; Ullmann's Encyclopedia of Industrial Chemistry, 5th edition, VCH Verlagsgesellschaft, Weinheim, 1985–1996, entry "vitamin K").

Recently, a novel therapeutic approach for the treatment and prophylaxis of thromboembolic disorders has been described. This novel therapeutic approach aims to inhibit factor Xa (cf. WO-A-99/37304; WO-A-99/06371; J. Hauptmann, J. Stürzebecher, Thrombosis Research 1999, 93, 203; F. Al-Obeidi, J. A. Ostrem, Factor Xa inhibitors by classical and combinatorial chemistry, DDT 1998, 3, 223; F. Al-Obeidi, J. A. Ostrem, Factor Xa inhibitors, Exp. Opin. Ther. Patents 1999, 9, 931; B. Kaiser, Thrombin and factor Xa inhibitors, Drugs of the Future 1998, 23, 423; A. Uzan, Antithrombotic agents, Emerging Drugs 1998, 3, 189; B.-Y. Zhu, R. M. Scarborough, Curr. Opin. Card. Pulm. Ren. Inv. Drugs 1999, 1 (1), 63). It has been shown that, in animal models, various both peptidic and nonpeptidic compounds are effective as factor Xa inhibitors.

Accordingly, it is an object of the present invention to provide novel substances for controlling disorders, which substances have a wide therapeutic spectrum.

In particular, they should be suitable for a more efficient prophylaxis and/or treatment of thromboembolic disorders, avoiding—at least to some extent—the disadvantages of the prior art described above, where the term "thromboembolic disorders" in the context of the present invention is to be understood as meaning, in particular, serious disorders, such as myocardial infarct, angina pectoris (including unstable angina), reocclusions and restenoses after angioplasty or aortocoronary bypass, stroke, transitory ischemic attacks, peripheral arterial occlusive disorders, pulmonary embolisms or deep venous thromboses.

It is another object of the present invention to provide novel anticoagulants which inhibit the blood coagulation factor Xa with increased selectivity, avoiding—at least to some extent—the problems of the therapeutic methods for thromboembolic disorders known from the prior art.

The present invention provides compounds of the formula (I)

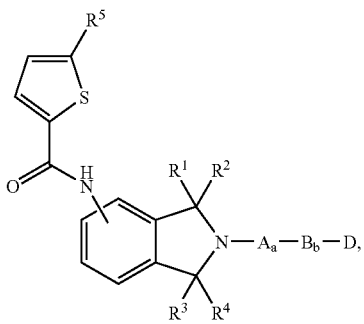

in which
R¹ and R² together represent O and
R³ and R⁴ together represent O, or
R¹ represents hydrogen, hydroxy or $(C_1-C_4)$-alkoxy,
R² represents hydrogen and
R³ and R⁴ together represent O, or
R¹ and R² together represent O,
R³ represents hydrogen, hydroxy or $(C_1-C_4)$-alkoxy and
R⁴ represents hydrogen,
R⁵ represents halogen, trifluoromethyl or methyl,
A represents $(C_1-C_4)$-alkanediyl which may be substituted by hydroxy or $(C_1-C_4)$-alkoxy,
a represents 0 or 1,
B represents a group

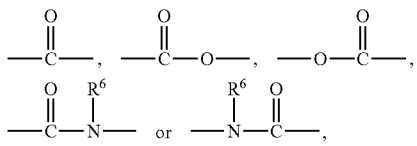

in which
R⁶ represents hydrogen or $(C_1-C_4)$-alkyl,
b represents 0 or 1,
D represents a 5- to 7-membered heterocyclyl,
which may be mono- or disubstituted, independently of one another, by hydroxy, carbamoyl, $(C_1-C_4)$-alkanoyl, $(C_3-C_7)$-cycloalkanoyl, $(C_3-C_7)$-cycloalkyl, 5- to 10-membered heterocyclyl, $(C_1-C_4)$-alkoxy-carbonyl, $(C_1-C_6)$-alkyl,
which for its part may be substituted by hydroxy, cyano, $(C_1-C_4)$-alkoxy, mono- or di-$(C_1-C_6)$-alkylamino, mono- or di-$(C_1-C_6)$-alkylaminocarbonyl, 5- to 10-membered heterocyclyl, 5- or 6-membered heterocyclylcarbonyl or 5- to 10-membered heteroaryl,
$(C_6-C_{10})$-aryl,
which for its part may be substituted by halogen, trifluoromethyl, nitro, $(C_1-C_4)$-alkyl or $(C_1-C_4)$-alkoxy,
5- to 10-membered heteroaryl,
which for its part may be substituted by cyano, amino or $(C_1-C_4)$-alkyl,
or 5- to 10-membered heteroarylcarbonyl,
$(C_1-C_6)$-alkyl,
which may be substituted by cyano, amino, mono- or di-$(C_1-C_6)$-alkylamino, amidino, 5- to 10-membered heteroaryl, by 5- to 10-membered heteroarylamino which is optionally substituted by halogen,
by 5- to 10-membered heterocyclyl which is optionally substituted by 5- to 10-membered heteroaryl, or by $(C_1-C_4)$-alkanoylamino,
or
5- to 10-membered heteroaryl,
which may be substituted by halogen or $(C_1-C_4)$-alkyl, and their salts, hydrates, hydrates of the salts and solvates.

Depending on the substitution pattern, the compounds of the formula (I) according to the invention may exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components.

Furthermore, certain compounds of the formula (I) can be present in tautomeric form. This is known to the person skilled in the art, and such compounds are likewise within the scope of the invention.

Salts of the compounds according to the invention are physiologically acceptable salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, trifluoroacetic acid, propionic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid or naphthalenedisulfonic acid.

Other possible salts are physiologically acceptable salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine or methyl-piperidine.

Moreover, the invention also embraces prodrugs of the compounds according to the invention. According to the invention, prodrugs are forms of the compounds of the formula (I) which for their part can be biologically active or inactive, but which can be converted into the corresponding biologically active form under physiological conditions (for example metabolically or solvolytically).

According to the invention, "hydrates" or "solvates" are forms of the compounds of the formula (I) which, in solid or liquid state, form a molecule compound or a complex by hydration with water or coordination with solvent molecules. Examples of hydrates are sesquihydrates, monohydrates, dihydrates or trihydrates. Equally suitable are the hydrates or solvates of salts of the compounds according to the invention.

Halogen represents fluorine, chlorine, bromine and iodine. Preference is given to chlorine, bromine or fluorine.

$(C_1-C_6)$-Alkyl represents a straight-chain or branched alkyl radical having 1 to 6 carbon atoms. Examples which may be mentioned are: methyl, ethyl, n-propyl, isopropyl, n-butyl, isobutyl and tert-butyl. The corresponding alkyl groups having fewer carbon atoms, such as, for example $(C_1-C_4)$-alkyl or $(C_1-C_3)$-alkyl, are derived analogously from this definition. In general, preference is given to $(C_1-C_3)$-alkyl.

The meaning of the corresponding component of other more complex substituents, such as, for example, in mono- or dialkylamino or mono- or dialkylaminocarbonyl, is likewise derived from this definition.

Monoalkylamino represents an amino group having an alkyl substituent as defined above. Dialkylamino represents an amino group having two identical or different alkyl substituents as defined above. Mono- or dialkylaminocarbonyl represents a mono- or dialkylamino group as defined above which is attached via a carbonyl group.

($C_1$–$C_4$)-Alkanediyl represents a straight-chain or branched alkanediyl radical having 1 to 4 carbon atoms. Preference is given to a straight-chain or branched alkanediyl radical having 1 to 3 carbon atoms. Examples which may be mentioned are: methanediyl, ethanediyl, propane-1,3-diyl, propane-1,2-diyl, propane-2,2-diyl, butane-1,4-diyl, butane-1,3-diyl.

($C_3$–$C_7$)-Cycloalkyl represents a cyclic alkyl radical having 3 to 7 carbon atoms. Examples which may be mentioned are: cyclopropyl, cyclobutyl, cyclopentyl, cyclohexyl or cycloheptyl. The corresponding cycloalkyl radicals having fewer carbon atoms, such as ($C_3$–$C_6$)-cycloalkyl, are derived from this definition. Preference is given to cyclopropyl, cyclopentyl and cyclohexyl.

The meaning of the corresponding component of other more complex substituents, such as, for example, cycloalkylamino, is likewise derived from this definition. Cycloalkylamino represents a cycloalkyl radical as defined above which carries, as substituent, an an amino group and is attached via the amino nitrogen atom.

($C_1$–$C_4$)-Alkanoyl represents a straight-chain or branched alkyl radical having 1 to 4 carbon atoms which carries, in the 1-position, a doubly attached oxygen atom and is attached via the 1-position. Examples which may be mentioned are: formyl, acetyl, propionyl, n-butyryl, i-butyryl.

The meaning of the corresponding component of other more complex substituents, such as, for example, cycloalkanoyl or alkanoylamino, is likewise derived from this definition. Cycloalkanoyl represents a cycloalkyl radical as defined above which, as substituent, carries a carbonyl group and is attached via this carbonyl group. Alkanoylamino represents an alkanoyl radical as defined above which, in the 1-position, carries, in addition to the doubly attached oxygen atom, additionally, as substituent, an amino group and is attached via this amino nitrogen atom.

($C_1$–$C_4$)-Alkoxy represents a straight-chain or branched alkoxy radical having 1 to 4 carbon atoms. Examples which may be mentioned are: methoxy, ethoxy, n-propoxy, isopropoxy, n-butoxy, isobutoxy, tert-butoxy. The corresponding alkoxy groups having fewer carbon atoms, such as, for example, ($C_1$–$C_3$)-alkoxy, are derived analogously from this definition. In general, preference is given to ($C_1$–$C_3$)-alkoxy.

($C_1$–$C_4$)-Alkoxycarbonyl represents a straight-chain or branched alkoxy radical having 1 to 4 carbon atoms which is attached via a carbonyl group. Examples which may be mentioned are: methoxycarbonyl, ethoxycarbonyl, n-propoxycarbonyl, isopropoxy-carbonyl and t-butoxycarbonyl. Preference is given to an alkoxycarbonyl radical having 1 or 2 carbon atoms.

($C_6$–$C_{10}$)-Aryl represents an aromatic radical having 6 to 10 carbon atoms. Examples which may be mentioned are: phenyl and naphthyl. In general, preference is given to phenyl.

5- to 10-membered heteroaryl represents a mono- or bicyclic, optionally benzo-fused aromatic heterocycle (heteroaromatic) which has up to 3 heteroatoms from the group consisting of N, O and S and which is attached via a ring carbon atom or a ring nitrogen atom of the heteroaromatic. Examples which may be mentioned are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl. The corresponding heteroaromatics having a smaller ring size, such as, for example, 5- or 6-membered heteroaryl, are derived analogously from this definition. In general, preference is given to 5- or 6-membered heteroaryl, such as, for example, pyridyl, pyrimidyl, pyridazinyl and pyrazinyl.

The meaning of the corresponding component of other more complex substituents, such as, for example, heteroarylcarbonyl, is likewise derived from this definition. Heteroarylcarbonyl represents a heteroaryl radical as defined above which, as substituent, carries a carbonyl group and is attached via the carbon atom of this carbonyl group.

The meaning of the corresponding component of other more complex substituents, such as, for example, heteroarylamino, is likewise derived from this definition. Heteroarylamino represents a heteroaryl radical as defined above which, as substituent, carries an amino group and is attached via the nitrogen atom of this amino group.

3- to 10-membered heterocyclyl represents a saturated or partially unsaturated mono- or bicyclic, optionally benzo-fused heterocycle which has up to 3 heteroatoms from the group consisting of S, N and O, and which is attached via a ring carbon atom or a ring nitrogen atom. Examples which may be mentioned are: oxiranyl, tetrahydrofuryl, pyrrolidinyl, pyrrolinyl, piperidinyl, 1,2-dihydropyridinyl, 1,4-dihydropyridinyl, piperazinyl, hexahydrodiazepinyl, morpholinyl, morpholinyl N-oxide, thiomorpholinyl, azepinyl and 1,4-diazepinyl. The corresponding heterocycles having a smaller ring size, such as, for example, 5- to 7-membered heterocycles or 5- or 6-membered heterocycles, are derived analogously from this definition. In general, preference is given to 5- to 7-membered heterocycles, such as piperidinyl, morpholinyl, hexahydrodiazepinyl, piperazinyl and pyrrolidinyl.

The meaning of the corresponding component of other more complex substituents, such as, for example, heterocyclylcarbonyl, is likewise derived from this definition. Heterocyclylcarbonyl represents a heterocyclyl radical as defined above which carries, as substituent, a carbonyl group and is attached via the carbon atom of this carbonyl group.

Preference is given to compounds of the formula (I)
in which
the thiophenecarboxylic acid substituent is attached to the phenyl ring in the ortho-position to the point of attachment of the fused heterocycle,
$R^1$ and $R^2$ together represent O and
$R^3$ and $R^4$ together represent O, or $R^1$ represents hydrogen, hydroxy, methoxy or ethoxy,
$R^2$ represents hydrogen and
$R^3$ and $R^4$ together represent O, or $R^1$ and $R^2$ together represent O,
$R^3$ represents hydrogen, hydroxy, methoxy or ethoxy and
$R^4$ represents hydrogen,
$R^5$ represents halogen or trifluoromethyl,
A represents ($C_1$–$C_4$)-alkanediyl, which may be substituted by hydroxy,
a represents 0 or 1, B represents a group

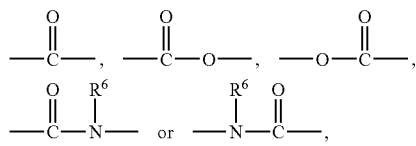

in which
R⁶ represents hydrogen,
b represents 0 or 1,
D represents a 5- to 7-membered heterocyclyl,
which may be mono- or disubstituted, independently of one another, by hydroxy, carbamoyl, acetyl, cyclopropanoyl, $(C_3-C_6)$-cycloalkyl, 5- to 10-membered heterocyclyl, $(C_1-C_3)$-alkyl,
which for its part may be substituted by hydroxy, methoxy, mono- or dimethylamino, mono- or di-$(C_1-C_3)$-alkylaminocarbonyl, 5- or 6-membered heterocyclyl, 5- or 6-membered heterocyclylcarbonyl or 5- or 6-membered heteroaryl,
phenyl,
which for its part may be substituted by fluorine, chlorine, trifluoromethyl, methyl or methoxy,
or 5- or 6-membered heteroaryl,
which for its part may be substituted by cyano, amino or methyl,
$(C_1-C_6)$-alkyl,
which may be substituted by amino, mono- or dimethylamino, amidino, 5- or 6-membered heteroaryl, 5- or 6-membered heteroaryl-amino, by 5- or 6-membered heterocyclyl which is optionally substituted by 5- or 6-membered heteroaryl, or by $(C_1-C_4)$-alkanoylamino,
or
represents 5- to 9-membered heteroaryl, and their salts, hydrates, hydrates of the salts and solvates.

Particular preference is given to compounds of the formula (I),
in which
the thiophenecarboxylic acid substituent is attached to the phenyl ring in the ortho-position to the point of attachment of the fused heterocycle,
$R^1$ and $R^2$ together represent O and
$R^3$ and $R^4$ together represent O,
or
$R^1$ represents hydrogen, hydroxy or methoxy
$R^2$ represents hydrogen and
$R^3$ and $R^4$ together represent O,
or
$R^1$ and $R^2$ together represent O,
$R^3$ represents hydrogen, hydroxy or methoxy and
$R^4$ represents hydrogen,
$R^5$ represents chlorine or bromine,
A represents methanediyl, ethanediyl or propane-1,3-diyl,
which radicals may be substituted by hydroxy,
a represents 0 or 1,
B represents a group

b represents 0 or 1,
D represents pyrrolidine, piperidine or piperazine,
which may be mono- or disubstituted, independently of one another,
by methyl, ethyl, n-propyl or isopropyl,
which for their part may be substituted by hydroxy or pyridyl,
or pyridyl,
which for its part may be substituted by amino or methyl,
or
$(C_1-C_3)$-alkyl,
which may be substituted by amidino, optionally pyridyl-substituted piperidinyl or acetylamino, and their salts, hydrates, hydrates of the salts and solvates.

The present invention also provides a process for preparing the compounds of the formula (I) according to the invention where
either
[A] compounds of the formula (II)

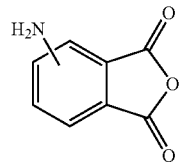

(II)

are converted
[A.1] with compounds of the formula (III)

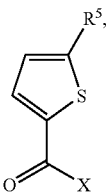

(III)

in which R⁵ is as defined above and X represents a leaving group, into compounds of the formula (IV)

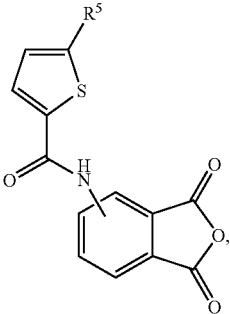

(IV)

in which R⁵ is as defined above, and these are subsequently
either
[A.1.1] converted with compounds of the formula (V)

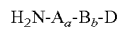

(V)

in which A, a, B, b and D are as defined above,
or
[A.1.2] converted with compounds of the formula (VI)

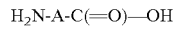

(VI)

in which A is as defined above, via the stage of compounds of the formula (VII)

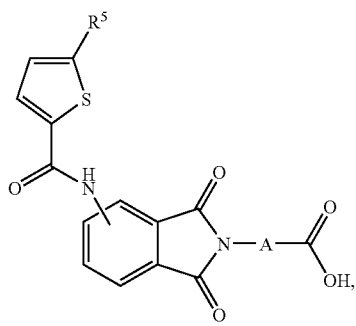
(VII)

in which A and R⁵ are as defined above, and subsequent reaction with amines or alcohols
into compounds of the formula (I)

or

[A.2] compounds of the formula (II)

are either

[A.2.1] converted with compounds of the formula (V)

or

[A.2.2] converted with compounds of the formula (VI) via the stage of compounds of the formula (VIII)

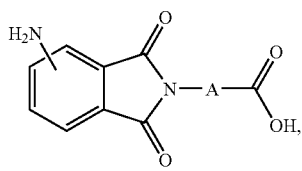
(VIII)

in which A is as defined above, and subsequent reaction with amines or alcohols
into compounds of the formula (IX)

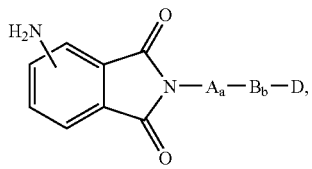
(IX)

in which A, B and D are as defined above, and then converted with compounds of the formula (III) into compounds of the formula (I)

or

[B] compounds of the formula (X)

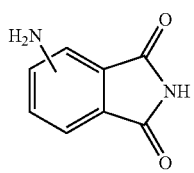
(X)

are converted

[B.1] with compounds of the formula (III) into compounds of the formula (XI)

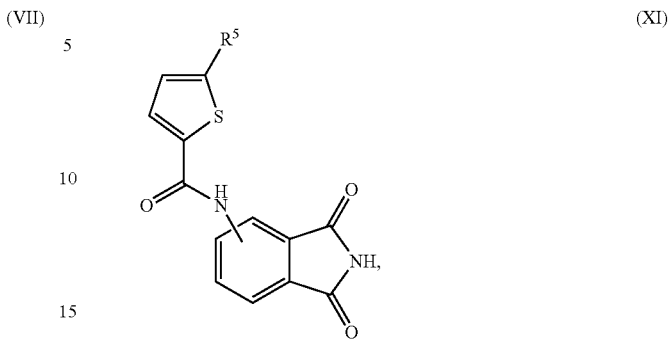
(XI)

in which R⁵ is as defined above, and these are subsequently converted with compounds of the formula (XII)

HO-A$_a$-B$_b$-D                (XII), in which A, a, B, b and D are as defined above, into compounds of the formula (I)

or

[B.2] with compounds of the formula (XII) into compounds of the formula (XIII)

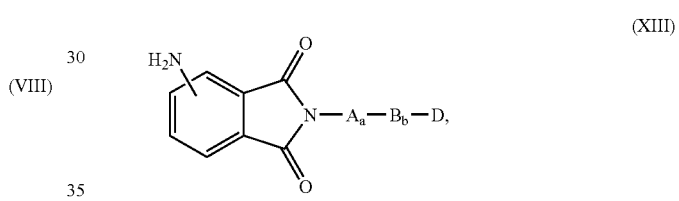
(XIII)

in which A, a, B, b and D are as defined above, and these are subsequently converted with compounds of the formula (III)

into compounds of the formula (I)

or

[C] compounds of the formula (XIV)

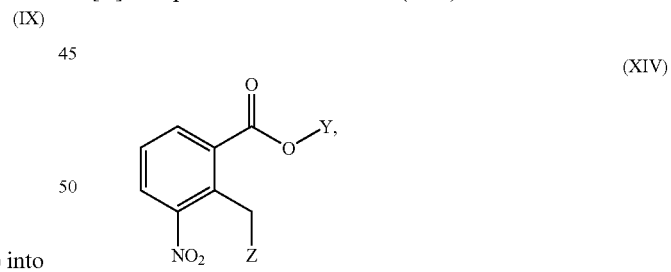
(XIV)

in which Y represents (C$_1$–C$_4$)-alkyl and Z represents a leaving group, are converted with compounds of the formula (V) into compounds of the formula (XV)

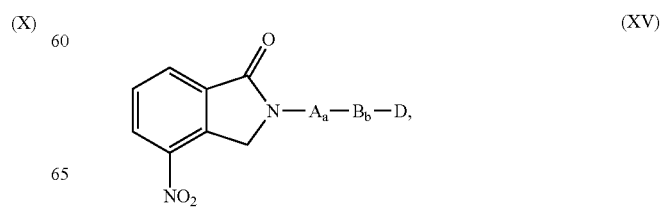
(XV)

in which A, a, B, b and D are as defined above, then converted by reduction of the nitro group into compounds of the formula (XVI)

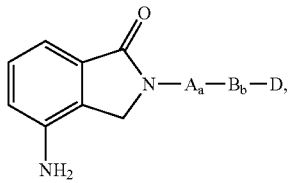
(XVI)

in which A, a, B, b and D are as defined above, and then converted with compounds of the formula (III) into compounds of the formula (I), where the resulting compounds of the formula (I) may, if appropriate, subsequently be subjected to further derivatizations which can be carried out by customary methods.

The process according to the invention can be illustrated in an exemplary manner by the formula scheme below:

-continued

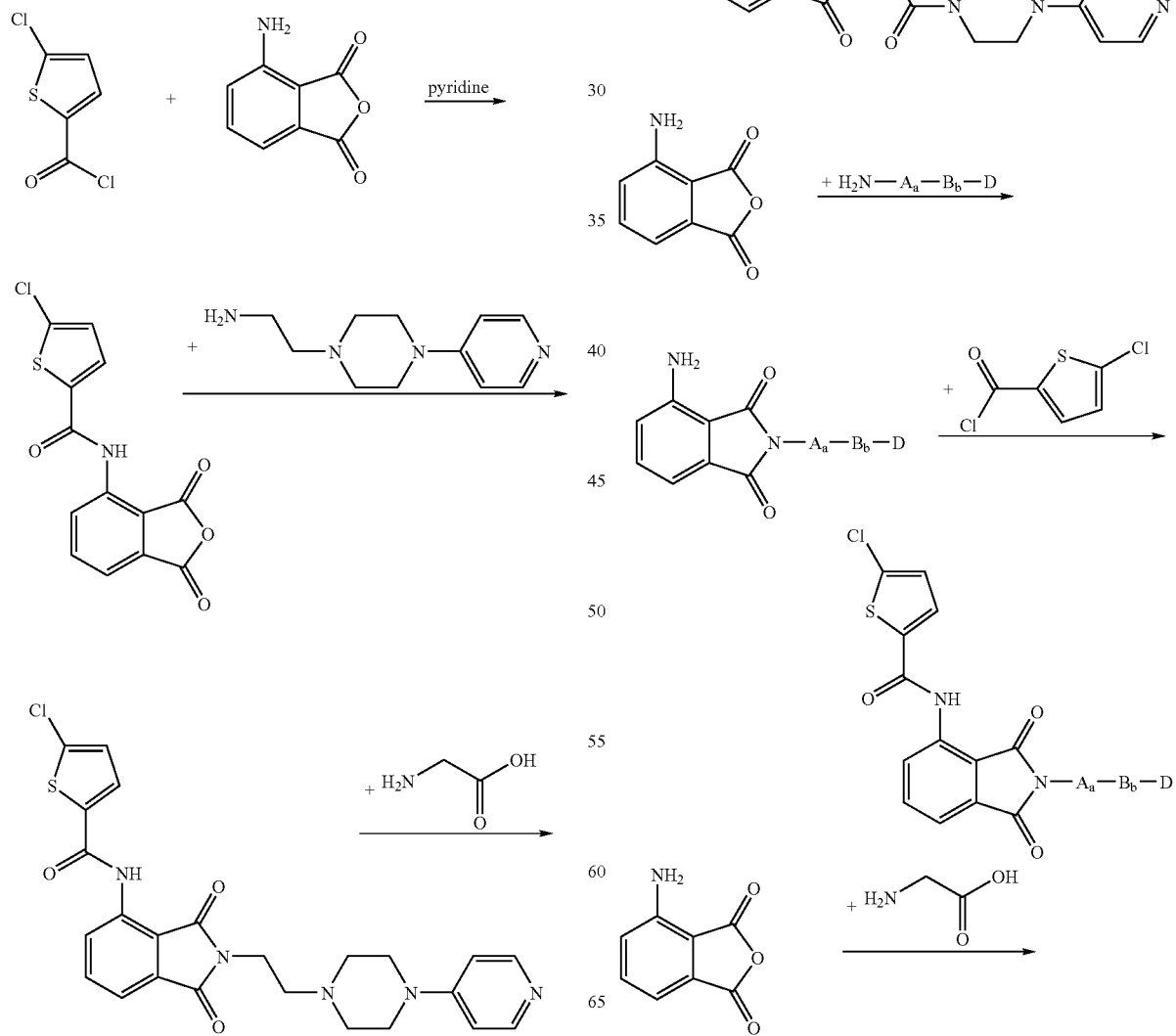

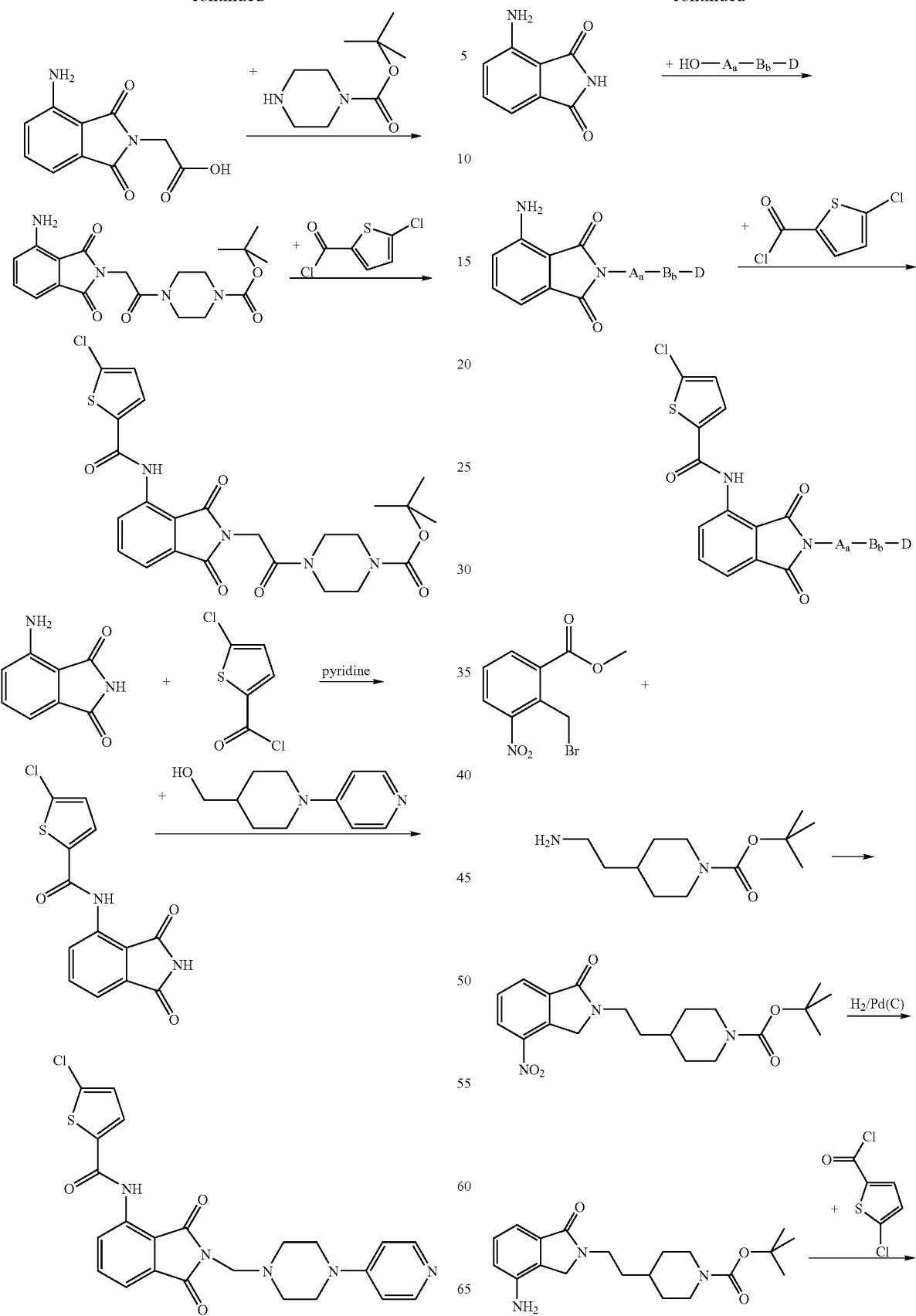

-continued

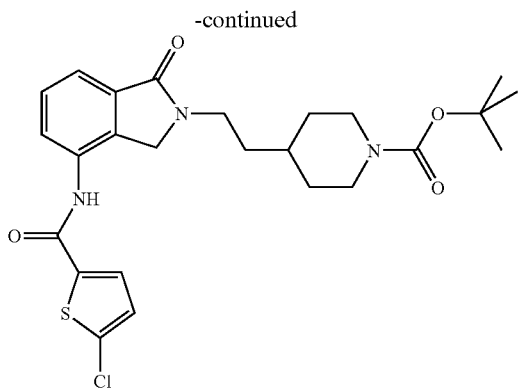

Solvents suitable for the process according to the invention are all organic solvents which are inert under the reaction conditions, or water. These include alcohols, such as methanol, ethanol and isopropanol, ketones, such as acetone and methylethylketone, acyclic and cyclic ethers, such as diethyl ether, tetrahydrofuran and dioxane, esters, such as ethyl acetate or butyl acetate, hydrocarbons, such as benzene, xylene, toluene, hexane or cyclohexane, acetic acid, dimethylformamide, acetonitrile, pyridine, dimethyl sulfoxide (DMSO), chlorinated hydrocarbons, such as dichloromethane, chlorobenzene or dichloroethane. It is also possible to use mixtures of the solvents mentioned above.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate or sodium bicarbonate or potassium bicarbonate, or sodium methoxide or potassium methoxide or sodium ethoxide or potassium ethoxide or potassium tert-butoxide, or else amides, such as sodium amide, lithium bis(trimethylsilyl)amide or lithium diisopropylamide, or organometallic compounds, such as butyllithium or phenyllithium, or else also amines, such as trialkylamines, for example triethylamine, N-methylmorpholine (NMM), N-methylpiperidine, diisopropylethylamine (Hünig base) or 4-N,N-dimethylaminopyridine (DMAP) or pyridine.

The process according to the invention can be carried out at atmospheric, elevated or reduced pressure (for example in the range from 0.5 to 5 bar). In general, the process is carried out at atmospheric pressure.

The reaction with thiophenecarboxylic acid derivatives of the formula (III) as in process step [A. 1]: (II)+(III)→(IV); second process step [A.2]: (IX)+(III)→(I); first process step [B.2]: (X)+(III)→(XI); second process step [B.2]: (XIII)+(III)→(I) and third process step [C]: (XVI)+(III)→(I) is generally carried out in a temperature range of from −78° C. to +120° C., preferably in the range from −78° C. to +60° C., in particular at from 0° C. to +50° C. The leaving group X used is, for example, a halogen, i.e. the corresponding acid chloride or acid bromide, or use is made of the corresponding acid anhydrides. Preference is given to the corresponding acid chloride. A preferred solvent is pyridine or tetrahydrofuran. If appropriate, 4-dimethylaminopyridine (4-DMAP) or triethylamine is added as base.

In process step [A. 1.1]: (IV)+(V)→(I) and process step [A.2.1]: (II)+(V)→(IX), phthalic anhydrides are reacted with primary amines to the corresponding phthalimides. Preferred solvent is acetic acid or dioxane. The reaction is generally carried out in a temperature range of from −78° C. to +150° C, preferably from 0° C. to +120° C., in particular at the reflux temperature of the solvent.

In process step [A.1.2]: (IV)+(VI)→(VII)→(I) and process step [A.2.2]: (II)+(VI)→(VIII)→(IX), phthalic anhydrides are initially reacted with amino acids to give the corresponding phthalimides (VII) and (IX), respectively. The preferred solvent is dioxane or acetic acid. The reaction is generally carried out in a temperature range of from −78° C. to +150° C., preferably from 0° C. to +120° C., in particular at the reflux temperature of the solvent.

In a second step, the acid function of the original amino acid is then derivatized by reaction with alcohols or amines to give the corresponding esters and amides, respectively. Preferred embodiments are, for example, the reaction in the solvent dichloromethane or dimethylformamide at room temperature in the presence of N'-(3-dimethylaminopropyl)-N-ethylcarbodiimide hydrochloride (EDC), 1-hydroxy-1H-benzotriazole hydrate (HOBT) and a base such as diisopropylethylamine (DIEA) or triethylamine.

In the second process step [B.1]: (XI)+(XII)→(I) and in the first process step [B.2]: (X)+(XII)→(XIII), phthalimides are derivatized in a nucleophilic substitution reaction with compounds of the formula (XII). Here, the hydroxy group in compounds of the formula (XII) is activated by reagents such as diethyl azodicarboxylate (DEAD)/PPh$_3$ (Mitsunobu reaction). The preferred solvent is tetrahydrofuran. The reaction is generally carried out in a temperature range of from −78° C. to +120° C., preferably at from 0° C. to room temperature.

The alkylation in the first process step [C]: (XIV)+(V)→(XV) is generally carried out in a temperature range of from −78° C. to +120° C., preferably at from +50° C. to +80° C. Suitable leaving groups Z in compounds of the formula (XI) are, for example: halogen, tosylate or mesylate, preferably bromine. The preferred solvent is dimethylformamide, the additional base used is, for example, triethylamine.

In the second process step [C]: (XIII)→(XIV), an aromatic nitro group is converted into the corresponding amine. The preferred solvent is methanol, ethanol, tetrahydrofuran or ethyl acetate, or a mixture of these solvents. The reaction is generally carried out in a temperature range of from −78° C. to +120° C., preferably at room temperature. Suitable processes are customary hydrogenation processes; preference is given to hydrogenating with hydrogen at atmospheric pressure in the presence of a catalyst, such as, for example, palladium-on-carbon [Pd(C); 10% by weight].

The compounds of the formulae (II), (III), (V), (VI), (X), (XII) and (XIV) are commercially available, known from the literature or can be prepared by customary methods known from the literature.

The compounds of the formula (I) according to the invention have an unforeseeable useful pharmacological activity spectrum and are therefore particularly suitable for the prophylaxis and/or treatment of disorders.

The compounds of formula (I) according to the invention are also suitable for the prophylaxis and/or treatment of disorders in combination with one or more active compounds. Suitable active compounds are in particular platelet aggregation inhibitors, anticoagulants, fibrinolytics, antilipemics, coronary therapeutics and/or vasodilators.

The compounds of the formula (I) according to the invention act in particular as anticoagulants and can therefore preferably be employed in medicaments for the prophylaxis and/or treatment of thromboembolic disorders. For the purpose of the present invention, "thromboembolic disorders" include, in particular, serious disorders such as myocardial infarct, angina pectoris (including unstable angina), reocclusions and restenoses after angioplasty or aortocoronary bypass, stroke, transitory ischemic attacks, peripheral arterial occlusion disorders, pulmonary embolisms or deep venous thromboses.

Furthermore, the compounds of the formula (I) according to the invention are also suitable for treating disseminated intravascular coagulation (DIC).

Finally, the compounds of the formula (I) according to the invention are also suitable for the prophylaxis and/or treatment of atherosclerosis and arthritis, and additionally also for the prophylaxis and/or treatment of Alzheimer's disease and cancer.

Furthermore, the present invention also includes a method for preventing blood coagulation in vitro, in particular in banked blood or biological samples which contain factor Xa, which method is characterized in that compounds of the formula (I) are added.

The compounds of the formula (I) according to the invention act in particular as selective inhibitors of the blood coagulation factor Xa and do not inhibit, or only inhibit at considerably higher concentrations, other serine proteases as well, such as thrombin, plasmin or trypsin.

In the context of the present invention, inhibitors of the blood coagulation factor Xa in which the $IC_{50}$ values for the factor Xa inhibition are lower by a factor of 100, preferably by a factor of 500, in particular by a factor of 1000, than the $IC_{50}$ values for the inhibition of other serine proteases, in particular thrombin, plasmin and trypsin, are referred to as being "selective", where with a view to the test methods for selectivity, reference is made to the test methods of Examples A-1) a.1) and a.2) described below.

All customary administration forms are suitable for administration of the compounds according to the invention. Administration is preferably carried out orally, lingually, sublingually, buccally, rectally, locally, for example via implants or stents, or parenterally (i.e. bypassing the intestinal tract, that is intravenously, intraarterially, intracardially, intracutaneously, subcutaneously, transdermally, intraperitoneally or intramuscularly). Particularly suitable are oral and intravenous administration. Very particular preference is given to oral administration, this being a further advantage with respect to the prior-art therapy of thromboembolic disorders.

The novel active compounds of the formula (I) can be converted in a known manner into the customary formulations, such as tablets, sugar-coated tablets, pills, granules, aerosols, syrups, emulsions, suspensions and solutions, using inert non-toxic pharmaceutically suitable excipients or solvents. Here, the therapeutically active compound should in each case be present in a concentration of from about 0.1 to 95% by weight, preferably from 0.5 to 90% by weight, in particular from 1 to 85% by weight, of the total mixture, i.e. in amounts which are sufficient in order to achieve the dosage range indicated.

In spite of this, if appropriate, it may be necessary to depart from the amounts mentioned, namely depending on the body weight or on the type of administration route, on the individual response to the medicament, on the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual administrations over the course of the day.

The formulations are prepared, for example, by extending the active compounds with solvents and/or excipients, if appropriate using emulsifiers and/or dispersants, it being possible, for example if the diluent used is water, optionally to use organic solvents as auxiliary solvents.

In general it has proved advantageous in the case of intravenous administration to administer amounts from approximately 0.001 to 10 mg/kg, preferably approximately 0.01 to 10 mg/kg, in particular approximately 0.1 to 8 mg/kg, of body weight to achieve effective results.

In general, it has proved advantageous in the case of oral administration to administer amounts from approximately 0.01 to 50 mg/kg, preferably approximately 0.1 to 10 mg/kg, in particular approximately 0.5 to 8 mg/kg, of body weight to achieve effective results.

In spite of this, if appropriate, it may be necessary in the case of intravenous or oral administration to depart from the amounts mentioned, namely depending on the body weight or on the type of administration route, on the individual response to the medicament, on the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these over the course of the day, namely into several individual doses or as a continuous infusion.

Compared to the conventional preparations for treating thromboembolic disorders, the compounds of the formula (I) according to the invention—including the compounds excluded by disclaimer from the chemical product protection—are distinguished in particular by the fact that a greater therapeutic range is achieved by the selective inhibition of factor Xa. For the patient, this means a lower risk of bleeding, and for the treating physician, this means that the patient is easier to adjust. Moreover—owing to the mechanism—the onset of action is more rapid. Above all, however, the compounds according to the invention permit an oral administration form, which is a further advantage of the therapy with the compounds according to the invention.

The present invention is illustrated by the examples below.

A EVALUATION OF THE PHYSIOLOGICAL ACTIVITY

1. General Test Methods

The particularly advantageous biological properties of the compounds according to the invention can be determined by the following methods.

a) Test Description (in vitro)

a.1) Determination of the Factor Xa Inhibition

The enzymatic activity of human factor Xa (FXa) was measured using the conversion of a chromogenic substrate specific for FXa. Factor Xa cleaves p-nitroaniline from the chromogenic substrate. The determinations were carried out in microtitre plates as follows.

The test substances, in various concentrations, were dissolved in DMSO and incubated at 25° C. with human FXa (0.5 mmol/l dissolved in 50 mmol/l of tris buffer [C,C,C-tris(hydroxymethyl)-aminomethane], 150 mmol/l of NaCl, 0.1% BSA (bovine serum albumin), pH=8.3) for 10 minutes. Pure DMSO was used as control. The chromogenic substrate (150 μmol/l of Pefachrome® FXa from Pentapharm) was then added. After an incubation time of 20 minutes at 25° C., the extinction at 405 nm was determined. The extinctions of the test mixtures containing test substance were compared with the control mixtures without test substance, and the $IC_{50}$ values were calculated from these data.

a.2) Determination of the Selectivity

To assess selective FXa inhibition, the test substances were examined for their inhibition of other human serine proteases such as thrombin, trypsin and plasmin. To determine the enzymatic activity of thrombin (75 mU/ml), trypsin (500 mU/ml) and plasmin (3.2 mmol/l), these enzymes were dissolved in tris buffer (100 mmol/l, 20 mmol/l $CaCl_2$, pH=8.0) and incubated with test substance or solvent for 10 minutes. The enzymatic reaction was then started by adding the corresponding specific chromogenic substrates (Chromozym Thrombin® from Boehringer Mannheim, Chromozym Trypsin® from Boehringer Mannheim, Chromozym Plasmin® from Boehringer Mannheim) and the extinction at 405 nm was determined after 20 minutes. All determinations were carried out at 37° C. The extinctions of the test mixtures containing test substance were compared with the control samples without test substance, and the $IC_{50}$ values were calculated from these data.

a.3) Determination of the Anticoagulant Action

The anticoagulant action of the test substances was determined in vitro in human plasma. To this end, human blood was drawn off in a mixing ratio of sodium citrate/blood of 1/9 using a 0.11 molar sodium citrate solution as receiver. Immediately after the blood had been drawn off, it was mixed thoroughly and centrifuged at about 2000 g for 10 minutes. The supernatant was pipetted off. The prothrombin time (PT, synonyms: thromboplastin time, quick test) was determined in the presence of varying concentrations of test substance or the corresponding solvent using a commercial test kit (Neoplastin® from Boehringer Mannheim). The test compounds were incubated with the plasma at 37° C. for 10 minutes. Coagulation was then started by addition of thromboplastin, and the time when coagulation occurred was determined. The concentration of test substance which effected a doubling of the prothrombin time was determined.

b) Determination of the Antithrombotic Activity (in vivo)

b.1) Arteriovenous Shunt Model (Rat)

Fasting male rats (strain: HSD CPB:WU) having a weight of 200–250 g were anaesthetized using a Rompun/Ketavet solution (12 mg/kg/50 mg/kg). Thrombus formation was initiated in an arteriovenous shunt in accordance with the method described by Christopher N. Berry et al., Br. J. Pharmacol. (1994), 113, 1209–1214. To this end, the left jugular vein and the right carotid artery were exposed. The two vessels were connected by an extracorporeal shunt using a polyethylene tube (PE 60) of a length of 10 cm. In the middle, this polyethylene tube was attached to a further polyethylene tube (PE 160) of a length of 3 cm which contained a roughened nylon thread which had been arranged to form a loop, to form a thrombogenic surface. The extracorporeal circulation was maintained for 15 minutes. The shunt was then removed and the nylon thread with the thrombus was weighed immediately. The weight of the nylon thread on its own had been determined before the experiment was started. Before the extracorporeal circulation was set up, the test substances were administered to the animals while awake either intravenously via the tail vein or orally using a pharyngeal tube.

b.2) Arterial Thrombosis Model (Rat)

Male fasting rats (strain: HSD CPB: WU) were anaesthetized as described above. On average, the rats had a weight of about 200 g. The left carotid artery was exposed (about 2 cm). The formation of an arterial thrombus was induced by mechanical injury to the blood vessel in accordance with the method described by K. Meng et al., Naunyn-Schmiedeberg's Arch. Pharmacol. (1977), 301, 115–119. To this end, the exposed carotid artery was clamped from the blood flow, cooled to −12° C. in a metal trough for 2 minutes and, to standardize the size of the thrombi, simultaneously compressed using a weight of 200 g. The blood flow was then additionally reduced by a clip which was placed around the carotid artery distally from the injured section of the vessel. The proximal clamp was removed, and the wound was closed and re-opened after 4 hours to remove the injured section of the vessel. The section of the vessel was opened longitudinally and the thrombus was removed from the injured section of the vessel. The moist weight of the thrombi was determined immediately. The test substances were administered to the animals while awake at the beginning of the experiment, either intravenously via the tail vein or orally using a pharyngeal tube.

b.3) Venous Thrombosis Model (Rat)

Male fasting rats (strain: HSD CPB: WU) were anaesthetized as described above. On average, the rats had a weight of about 200 g. The left jugular vein was exposed (about 2 cm). The formation of a venous thrombus was induced by mechanical injury to the blood vessel in accordance with the method described by K. Meng et al., Naunyn-Schmiedeberg's Arch. Pharmacol. (1977), 301, 115–119. To this end, the jugular vein was clamped from the blood flow, cooled to −12° C. in a metal trough for 2 minutes and, to standardize the size of the thrombi, simultaneously compressed using a weight of 200 g. The blood flow was re-opened and the wound was closed. After 4 hours, the wound was re-opened to remove the thrombi from the injured sections of the vessel. The moist weight of the thrombi was determined immediately. The test substances were administered to the animals while awake at the beginning of the experiment, either intravenously via the tail vein or orally using a pharyngeal tube.

B PREPARATION EXAMPLES

The following abbreviations are used in the examples:

DIEA=N,N-Diisopropylethylamine
DMAP=4-N,N-Dimethylaminopyridine
DMF=Dimethylformamide
EDCI=N'-(3-Dimethylaminopropyl)-N-ethylcarbodiimide×HCl
EtOH=Ethanol
HOBt=1-Hydroxy-1H-benzotriazole×$H_2O$
rt=Retention time
RT=Room temperature
TFA=Trifluoroacetic acid
THF=Tetrahydrofuran
Tol=Toluene HPLC Parameters:

Method 1: Column: Kromasil C18, L-R temperature: 30° C., flow rate=0.75 mlmin$^{-1}$, mobile phase: A=0.01 M $HClO_4$, B=$CH_3CN$, gradient: →0.5 min 98% A→4.5 min 10% A→6.5 min 10% A Method 2: Column: Kromasil C18 60*2, L-R temperature: 30° C., flow rate=0.75 mlmin⁻¹, mobile phase A=0.01 $H_3PO_4$, B=$CH_3CN$, gradient: →0.5 min 90% A→4.5 min 10% A→6.5 min 10% A Method 3: Column: Kromasil C18 60*2, L-R temperature: 30° C., flow rate=0.75 mlmin⁻¹, mobile phase: A=0.005 M $HClO_4$, B=$CH_3CN$, gradient: →0.5 min 98% A→4.5 min 10% A→6.5 min 10% A Method 4: Column: Symmetry C18 2.1×150 mm, column oven: 50° C., flow rate=0.6 mlmin⁻¹, mobile phase: A=0.6 g 30% strength HCl/1 water, B=$CH_3CN$, gradient: 0.0 min 90% A→4.0 min 10% A→9 min 10% A Method 5: Instrument Micromass Quattro LCZ Column Symmetry C18, 50 mm×2.1 mm, 3.5 μm, temperature: 40° C., flow rate=0.5 mlmin⁻¹, mobile phase A=$CH_3CN$+0.1% formic acid, mobile phase B=water+0.1% formic acid, gradient: 0.0 min 10% A→4 min 90% A→6 min 90% A Method 6: Instrument Micromass Platform LCZ Column Symmetry C18, 50 mm×2.1 mm, 3.5 μm, temperature: 40° C., flow rate=0.5 mlmin⁻¹, mobile phase A=$CH_3CN$+0.1% formic acid, mobile phase B=water+0.1% formic acid, gradient: 0.0 min 10% A→4 min 90% A→6 min 90% A Method 7: Instrument Micromass Quattro LCZ Column Symmetry C18, 50 mm×2.1 mm, 3.5 μm, temperature: 40° C., flow rate=0.5 mlmin⁻, mobile phase A=$CH_3CN$+0.1% formic acid, mobile phase B=water+0.1% formic acid, gradient: 0.0 min 5% A→1 min 5% A→5 min 90% A→6 min 90% A

SYNTHESIS EXAMPLES

Example 1

5-Chloro-N-(1,3-dioxo-1,3-dihydro-2-benzofuran-4-yl)-2-thiophenecarboxamide

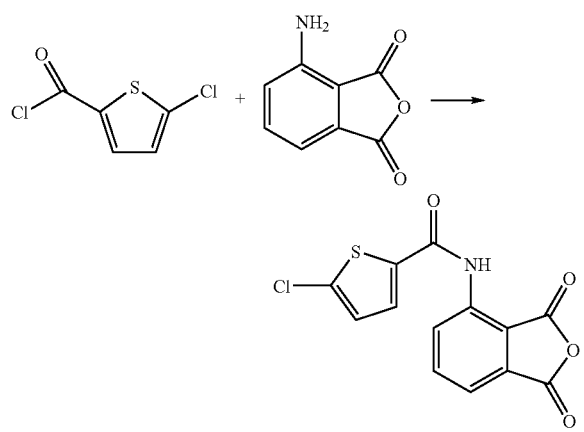

To prepare the required acid chloride, 27.77 g of 2-chloro-5-thiophenecarboxylic acid (0.171 mol) are suspended in 50 ml of thionyl chloride (0.685 mol) and stirred at 90° C. for 90 min (after 15 min, a clear solution is formed). The resulting solution is concentrated under reduced pressure, twice subjected to azeotropic distillation with toluene, dissolved in 60 ml of toluene and, over a period of 40 min and at 20° C., added dropwise to a solution of 17.98 g (110.2 mmol) of 3-aminophthalic anhydride in 200 ml of pyridine. The mixture is stirred at RT overnight, the pyridine is evaporated under reduced pressure and the residue is twice stirred with toluene and re-evaporated. 1l of ethyl acetate and 0.5l of $KH_2PO_4$ buffer (pH=4–5) are added and the mixture is then shaken vigorously and filtered off with suction, and the solids are washed with ethyl acetate, pressed thoroughly dry and dried under reduced pressure over $P_2O_5$. The mother liquor is extracted three times with ethyl acetate and evaporated and the residue is stirred with ethyl acetate and filtered off with suction. This gives a total of 19.77 g (58.3% of theory) of the target compound of m.p. 195° C.

Example 2

2-(4-{[(5-Chloro-2-thienyl)carbonyl]amino}-1,3-dioxo-1,3-dihydro-2H-isoindol-2-yl)acetic acid

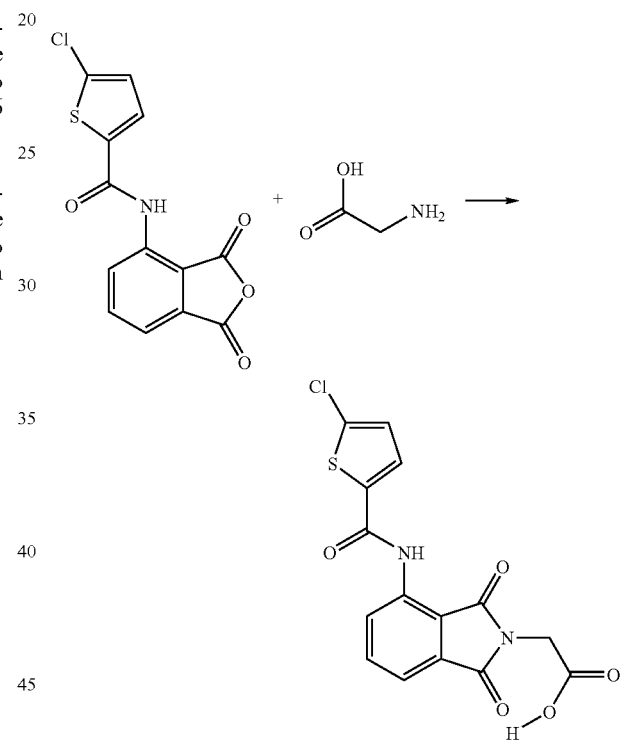

8.7 g (28.27 mmol) of 5-chloro-N-(1,3-dioxo-1,3-dihydro-2-benzofuran-4-yl)-2-thio-phenecarboxamide and 2.12 g (28.2 mmol) of glycine are boiled in 250 ml of dioxane over night. Another 6.3 g (83.9 mmol) of glycine are then added, and the mixture is boiled for a further 22 hours. After cooling, the solution is filtered off from glycine and the filtrate is concentrated under reduced pressure. This gives 10.2 g (98.9% of theory) of the target compound of melting point 247° C.

The following compound was prepared analogously from β-alanine:

Example 3

3-(4-{[(5-Chloro-2-thienyl)carbonyl]amino}-1,3-dioxo-1,3-dihydro-2H-isoindol-2-yl)propanoic acid in a yield of 99%, m.p. 194° C., Rf ($SiO_2$, EtOAc)=0.63.

Example 4

5-Chloro-N-(1,3-dioxo-2-{2-oxo-2-[4-(4-pyridinyl)piperazino]ethyl}-2,3-dihydro-1H-isoindol-4-yl)-2-thiophenecarboxamide

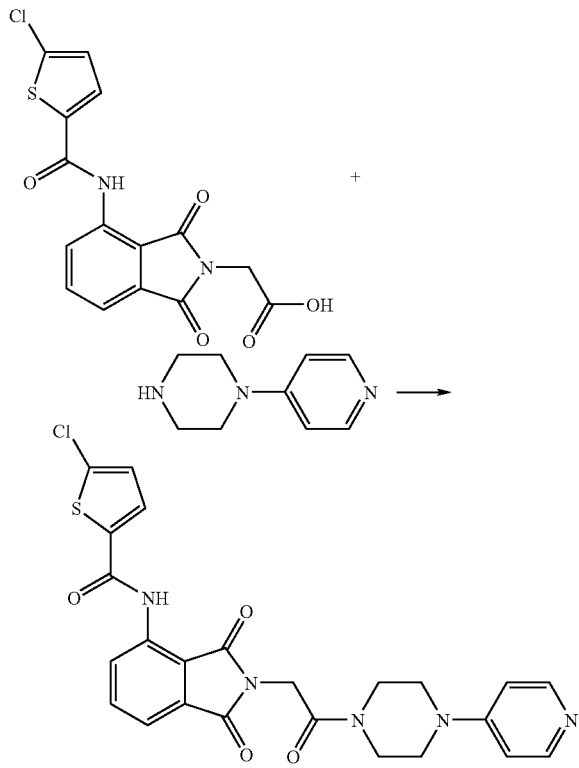

0.43 g (1.18 mmol) of 2-(4-{[(5-chloro-2-thienyl)carbonyl]amino}-1,3-dioxo-1,3-dihydro-2H-isoindol-2-yl)acetic acid is dissolved in 15 ml DMF, 0.2 g (1.3 equivalents) 1-hydroxy-1H-benzotriazole hydrate (HOBT) and 0.238 g of N'-(3-dimethylaminopropyl)-N-ethylcarbodiimide (EDCI) (1.3 equivalents) are added and 0.305 g (0.411 ml; 2 equivalents) of diisopropylethylamine (DIEA) is added dropwise at room temperature over a period of 15 min. The mixture is stirred at room temperature overnight, the suspension turning into a clear solution. Water is then added to the reaction mixture, the aqueous phase is extracted three times with ethyl acetate, the combined organic phases are dried and concentrated under reduced pressure and the residue is coevaporated three times with toluene. The residue is suspended in toluene, filtered and washed with toluene. Drying gives 0.458 g (76.4% of theory) of the target compound of m.p. 207° C.

The following compound was prepared analogously:

Example 5

5-Chloro-N-(1,3-dioxo-2-{3-oxo-3-[4-(4-pyridinyl)piperazino]propyl}-2,3-dihydro-1H-isoindol-4-yl)-2-thiophenecarboxamide m.p. 167° C.; Rf (SiO$_2$, toluene/ethanol=1:1) 0.2.

Furthermore, the compounds listed in the table below were prepared analogously from the corresponding substituted amine derivatives which for their part are obtainable, for example, by the routes described in WO97/03,072, U.S. Pat. No. 4,968,704 or by reacting halopyridines or halopyrimidines with diamines.

| Example | Structure | m.p. [° C.] |
|---|---|---|
| 6 | 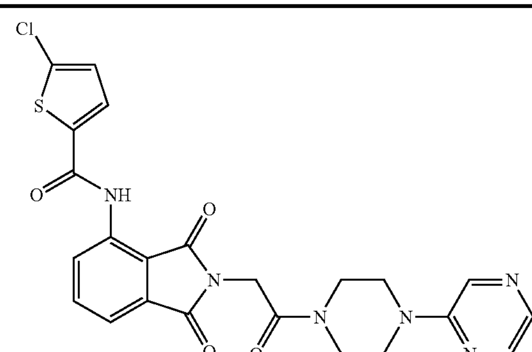 | 237 |
| 7 | 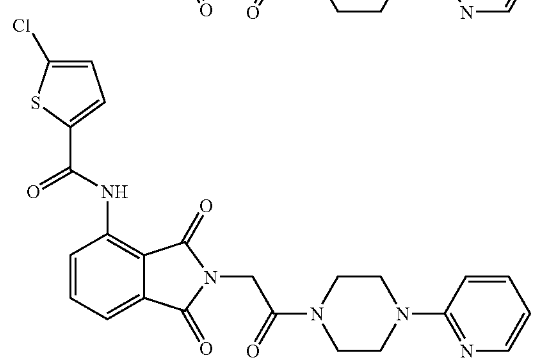 | 203 |

-continued

| Example | Structure | m.p. [° C.] |
|---|---|---|
| 8 | (structure) | 136 |
| 9 | (structure) | 169 (Z) |
| 10 | (structure) | 209 |
| 11 | (structure) | Oil<br>MS: 527.1 (M + H) |

-continued

| Example | Structure | m.p. [° C.] |
|---|---|---|
| 12 | 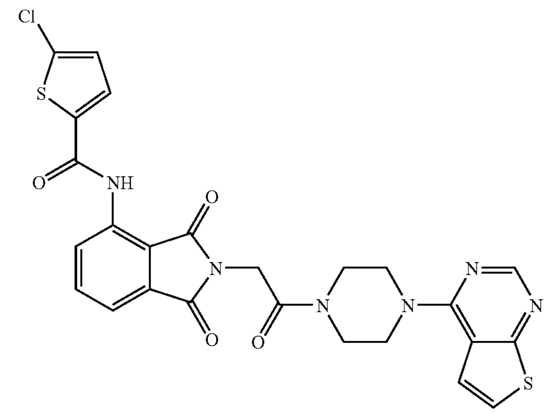 | 277 |
| 13 | 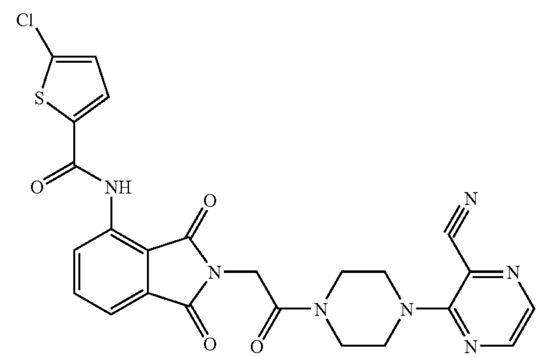 | 242 |
| 14 | 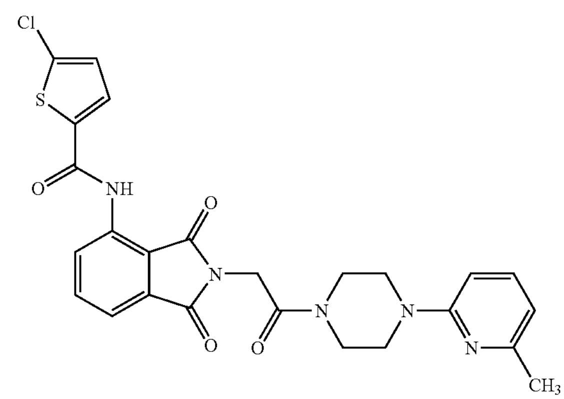 | 241 |
| 15 | 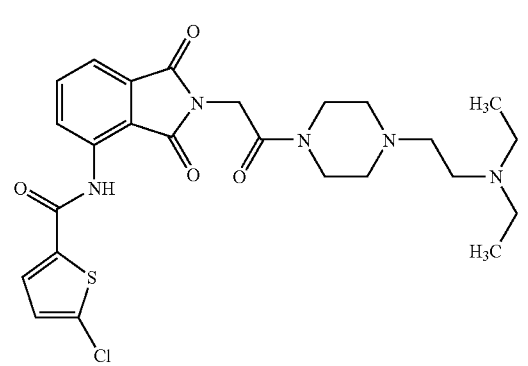 | Oil<br>MS: 532 (M + H) |

-continued

| Example | Structure | m.p. [° C.] |
|---|---|---|
| 16 | 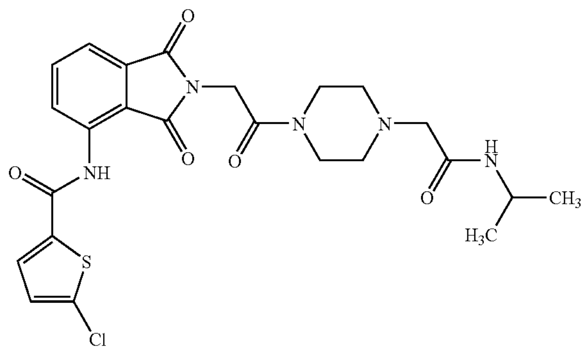 | 124 |
| 17 | 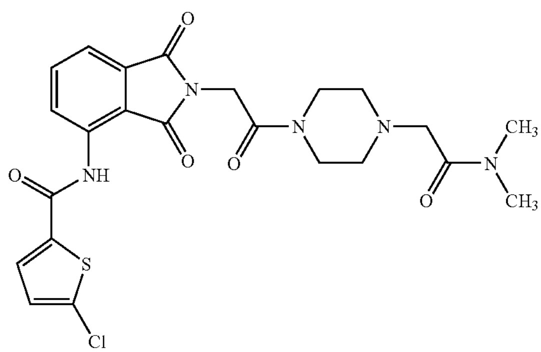 | 189 |
| 18 | 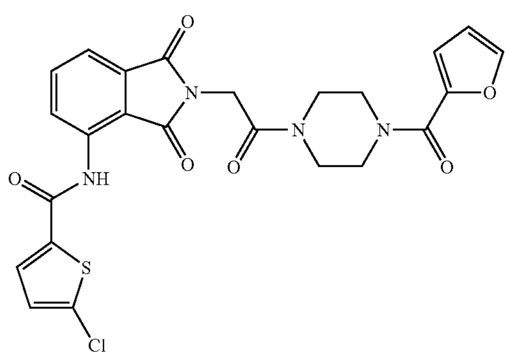 | Oil MS: 527 (M + H) |
| 19 | 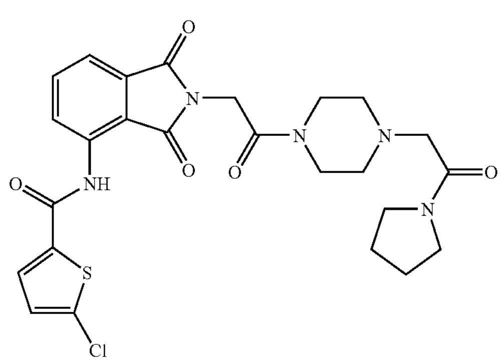 | 122 |

-continued

| Example | Structure | m.p. [° C.] |
|---|---|---|
| 20 | 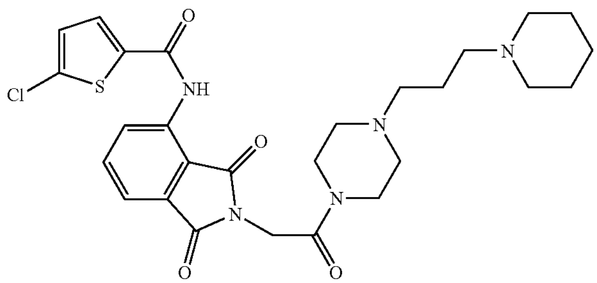 | 104 |
| 21 | 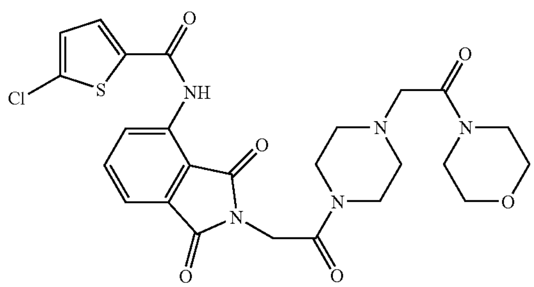 | 230 |
| 22 | 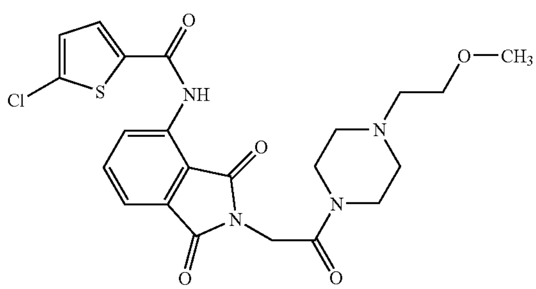 | 158 |
| 23 | 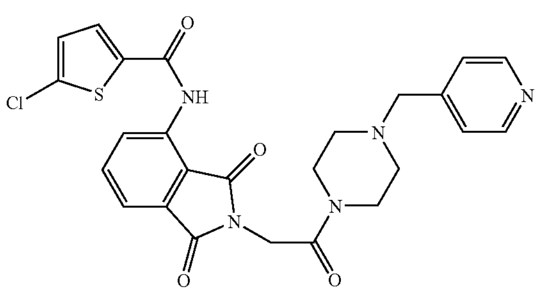 | Oil<br>MS: 524.2 (M + H) |
| 24 | 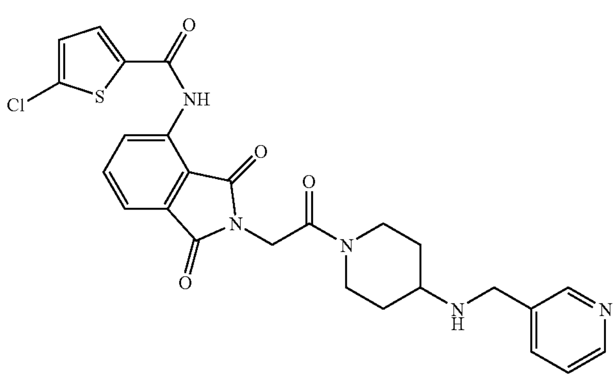 | 220 |

-continued

| Example | Structure | m.p. [° C.] |
| --- | --- | --- |
| 25 | 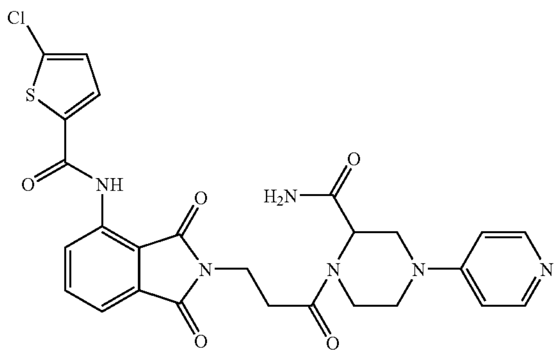 | Oil<br>MS: 567.1 (M + H) |
| 26 | 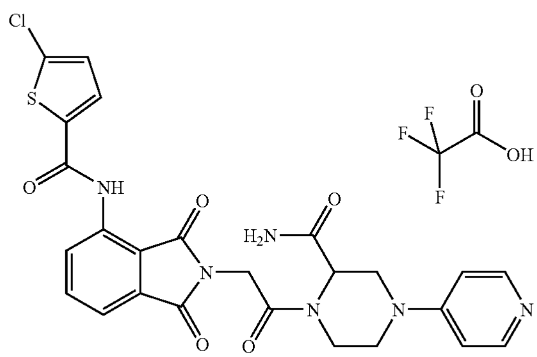 | Oil<br>MS: 553 (M + H) |
| 27 | 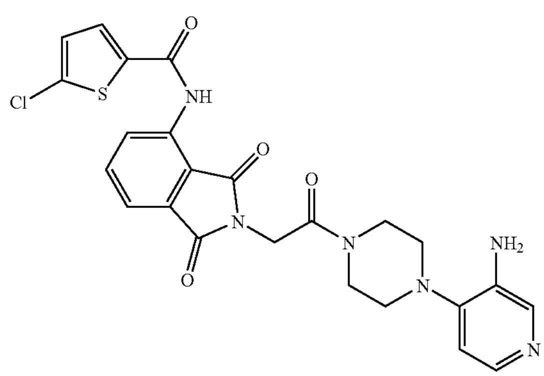 | 178 |
| 28 | 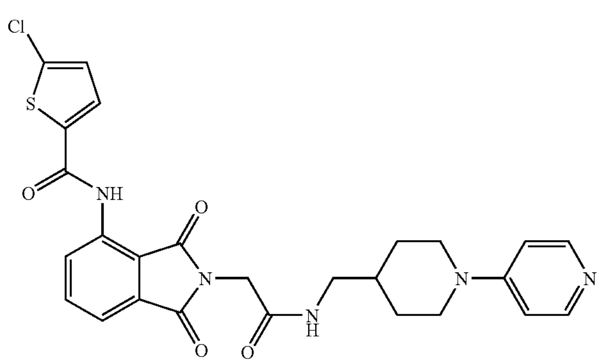 | 256 |

-continued
| Example | Structure | m.p. [° C.] |
|---|---|---|
| 29 | 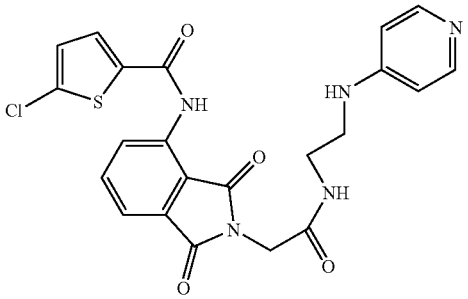 | >277<br>Rf(SiO$_2$, Toluene:<br>Ethanol 4:1)<br>0.82 |
| 30 | 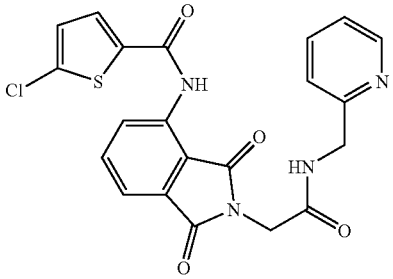 | 229<br>Rf(SiO$_2$, Toluene:<br>Ethanol 4:1)<br>0.66 |
| 31 | 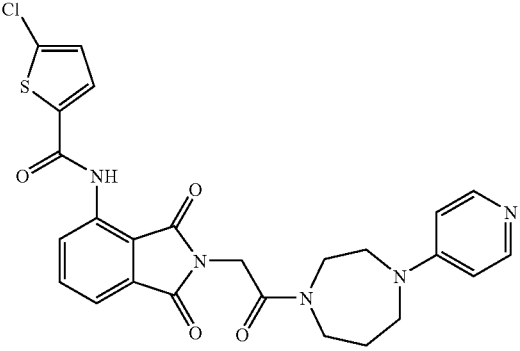 | Oil<br>MS: 524.3 (M + H) |
| 32 | 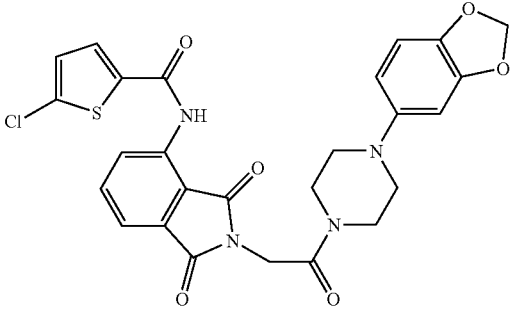 | 203 |

The following esters can also be obtained in an analogous manner using EDCI, HOBt, DIEA:

| Example | Structure | Starting material | Yield [%] | Rf(SiO$_2$) | m.p. [° C.] |
|---|---|---|---|---|---|
| 33 | 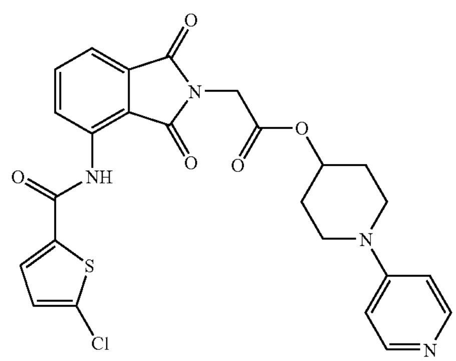 | 1-(4-pyridyl)-4-piperidinol [US4968704] | 32 | 0.27 Tol/EtOH = 1:1 | 229 |
| 34 | 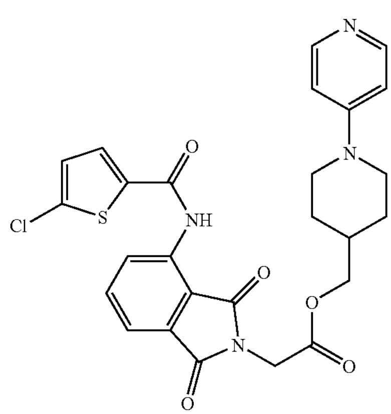 | 1-(4-pyridyl)-4-piperidinemethanol [US4968704] | 44 | 0.36 Tol/EtOH = 1:1 | Oil |
| 35 | 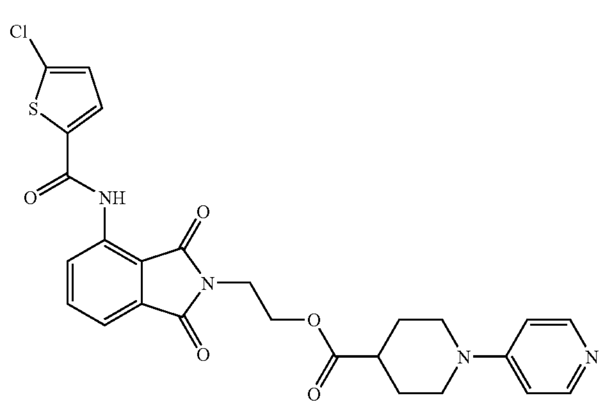 | 1-(4-pyridyl)-piperidine-4-carboxylic acid [Tetrahedron 1988, 44, 7095] | 83.7 | 0.22 Tol/EtOH = 4:1 | 124 |

Example 36

5-Chloro-N-(2-{2-[4-(hydroxymethyl)piperidino]-2-oxoethyl}-1,3-dioxo-2,3-dihydro-1H-isoindol-4-yl)-2-thiophenecarboxamide is obtained analogously m.p. 198° C., Rf(SiO$_2$, toluene/ethyl acetate=1:1): 0.79.

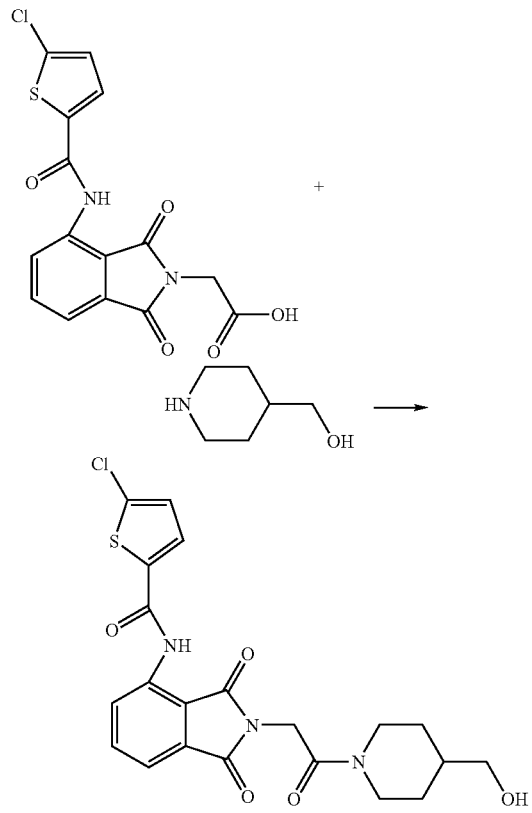

Example 37

2-(4-Amino-1,3-dioxo-1,3-dihydro-2H-isoindol-2-yl)-N-[2-(1H-imidazol-4-yl)ethyl]acetamide

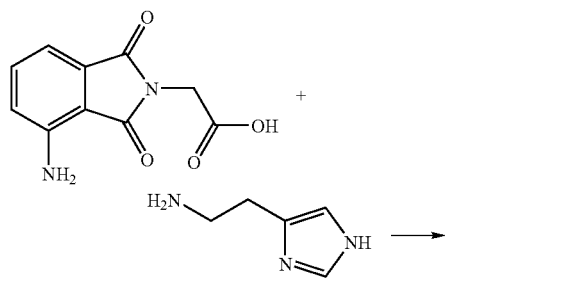

981 mg (4.455 mmol) of (4-amino-1,3-dioxo-1,3-dihydro-2H-isoindol-2-yl)acid (Caswell, Atkinson; *J. Org. Chem.*; 29; 1964; p. 3151) are suspended in 50 ml of dichloromethane. 902 mg (4.9 mmol) of histamine dihydrochloride, 1.025 g (5.35 mmol) of N'-(3-dimethylaminopropyl)-N-ethylcarbodiimide hydrochloride, 722mg (5.35 mmol) of 1-hydroxy-1H-benzotriazole and 3.1 ml (22.3 mmol) of triethylamine are added. The reaction mixture is stirred at RT overnight and then concentrated. The residue is triturated with water and filtered. The resulting solid is dissolved in dichloromethane/methanol and filtered, and the filtrate is concentrated, giving 539 mg (39% of theory) of the product.

MS=314 (M+H), LC (Method 4): rt=1.19 min.

Example 38 tert-Butyl 4-(2-{[(4-amino-1,3-dioxo-1,3-dihydro-2H-isoindol-2-yl)acetyl]-amino}ethyl)-1H-imidazole-1-carboxylate

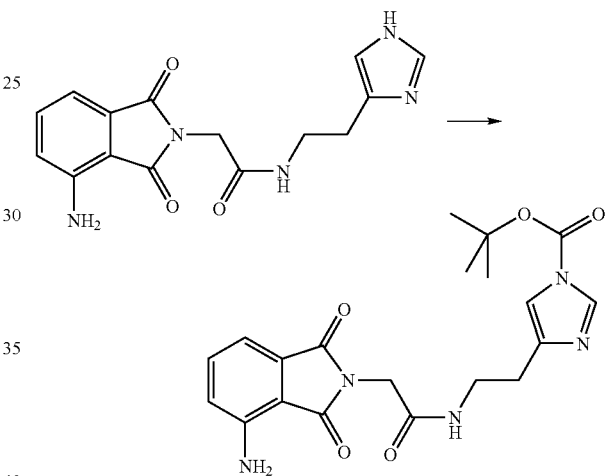

490 mg (1.56 mmol) of 2-(4-amino-1,3-dioxo-1,3-dihydro-2H-isoindol-2-yl)-N-[2-(1H-imidazol-4-yl)ethyl]acetamide are dissolved in 20 ml of DMF, and 0.65 ml (4.69 mmol) of triethylamine, 19 mg (0.16 mmol) of 4-DMAP and 375.5 mg (1.72 mmol) of di-tert-butyl dicarbonate are added. The reaction mixture is stirred at RT overnight, diluted with ethyl acetate and washed with saturated aqueous NaHCO$_3$ solution. The organic phase is dried over MgSO$_4$, filtered and concentrated. This gives 642 mg (99% of theory) of the product.

MS=414 (M+H), 314 (M+H—tert-BuCO$_2$).

Example 39 tert-Butyl 4-[(4-amino-1,3-dioxo-1,3-dihydro-2H-isoindol-2-yl)acetyl]-1-piperazinecarboxylate

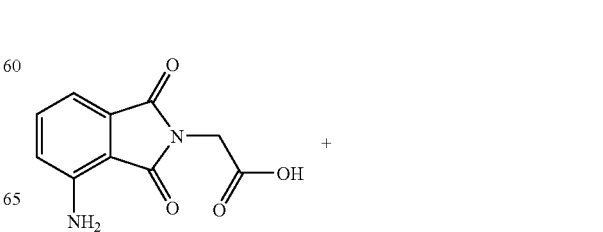

-continued

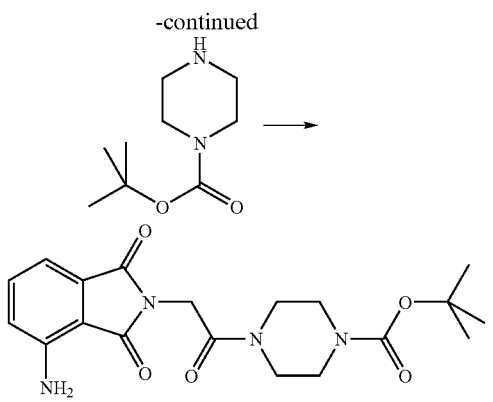

2 g (9.08 mmol) of (4-amino-1,3dioxo-1,3-dihydro-2H-isoindol-2-yl)acetic acid, 1.692 g (9.08 mmol) of tert-butyl 1-piperazinecarboxylate, 1.916 g (10 mmol) of N-(3-dimethylaminopropyl)-N-ethylcarbodiimide hydrochloride, 1.35 g (10 mmol) of 1-hydroxy-1H-benzotriazole and 3.8 ml (27 mmol) of triethylamine are stirred in 200 ml of dichloromethane at RT overnight. The reaction mixture is then washed with sat. aqu. NaHCO₃ solution, dried over MgSO₄, filtered and concentrated. The crude product (3.05 g) can be used without further purification for the next step or, if required, be chromatographed on silica gel (CH₂Cl₂/EtOH=1/0 to 2/1+0.1% conc. aqueous ammonia solution) for purification.

MS=389 (M+H), LC (Method 6): rt=3.57 min.

The following compounds were prepared analogously:

Example 40

From 3-(4-amino-1,3-dioxo-1,3-dihydro-2H-isoindol-2-yl)propanoic acid (Caswell, Yang; *J. Chem. Eng. Data;* 13; 1968; p. 291) and tert-butyl 1-piperazinecarboxylate:

tert-Butyl 4-[3-(4-amino-1,3-dioxo-1,3-dihydro-2H-isoindol-2-yl)propanoyl]-1-piperazinecarboxylate MS=403 (M+H), LC (Method 6): rt=3.58 min.

Example 41

From 3-(4-amino-1,3-dioxo-1,3-dihydro-2H-isoindol-2-yl)propanoic acid and morpholine:

4-Amino-2-[3-(4-morpholinyl)-3-oxopropyl]-1H-isoindole-1,3(2H)-dione

MS=304 (M+H), LC (Method 6): rt=2.57 min.

Example 42

5-Chloro-N-{1,3-dioxo-2-[2-oxo-2-(1-piperazinyl)ethyl]-2,3-dihydro-1H-isoindol-4-yl)-2-thiophenecarboxamide

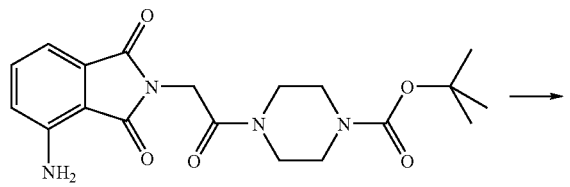

-continued

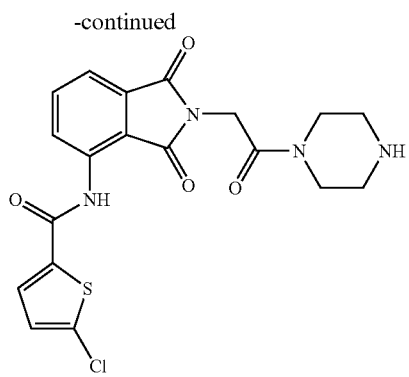

2.29 g (5.26 mmol) of tert-butyl 4-[(4-amino-1,3-dioxo-1,3-dihydro-2H-isoindol-2-yl)acetyl]-1-piperazinecarboxylate are dissolved in 20 ml of pyridine, and 1.143 g (6.31 mmol) of 5-chloro-2-thiophenecarbonyl chloride and 67 mg (0.55 mmol) of 4-DMAP are added. The reaction mixture is heated to 50° C. for 2 h, a further 500 µl of 5-chlor-2-thiophenecarbonyl chloride are then added and the mixture is stirred at 50° C. for 3 h. The reaction mixture is then concentrated and the residue is taken up in methylene chloride, washed with water and sat. sodium bicarbonate solution, dried over magnesium sulfate, filtered and concentrated. The crude product can be purified by chromatography on silica gel (CH₂Cl₂/EtOH/conc. aqueous ammonia solution).

The product of the acylation is dissolved in 150 ml of methylene chloride, and a mixture of 10 ml of trifluoroacetic acid and 40 ml of methylene chloride is slowly added at 0° C. The reaction mixture is slowly warmed to room temperature and stirred overnight. The reaction mixture is then concentrated and the crude product is chromatographed on silica gel (CH₂Cl₂/EtOH/conc. aqueous ammonia solution=20/1/0.05). This gives 1.17 g (51 % of theory) of the product.

MS=433 (M+H), LC (Method 4): rt=3.01 min.

The following compounds were obtained analogously by reaction with 5-chloro-2-thiophenecarbonyl chloride and, if appropriate, subsequent removal of the tert-butoxycarbonyl protective group:

Example 43

From tert-butyl 4-(2-{[(4-amino-1,3-dioxo-1,3-dihydro-2H-isoindol-2-yl)acetyl]-amino}ethyl)-1H-imidazole-1-carboxylate:

5-Chloro-N-[2-(2-{[2-(1H-imidazol-4-yl)ethyl]amino}-2-oxoethyl)-1,3-dioxo-2,3-dihydro-1H-isoindol-4-yl]-2-thiophenecarboxamide MS=458 (M+H), LC (Method 6): rt=2.86 min.

Example 44

From tert-butyl 4-[3-(4-amino-1,3-dioxo-1,3-dihydro-2H-isoindol-2-yl)propanoyl]-1-piperazinecarboxylate:

5-Chloro-N-{1,3-dioxo-2-[3-oxo-3-(1-piperazinyl)propyl]-2,3-dihydro-1H-isoindol-4-yl}-2-thiophenecarboxamide MS=447 (M+H), LC (Method 4): rt=3.06 min.

Example 45

From 4-amino-2-[3-(4-morpholinyl)-3-oxopropyl]-1H-isoindole-1,3(2H)-dione:

5-Chloro-N-{2-[3-(4-morpholinyl)-3-oxopropyl]-1,3-dioxo-2,3-dihydro-1H-isoindol-4-yl}-2-thiophenecarboxamide MS=448 (M+H), RT (Method 5)=4.11 min.

Example 46

N-{2-[3-(4-Acetyl-1-piperazinyl)-3-oxopropyl]-1,3-dioxo-2,3-dihydro-1H-isoindol-4-yl}-5-chloro-2-thiophenecarboxamide

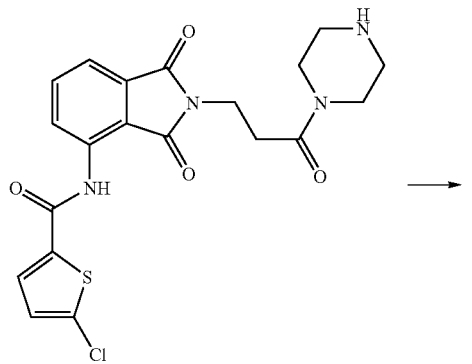

→

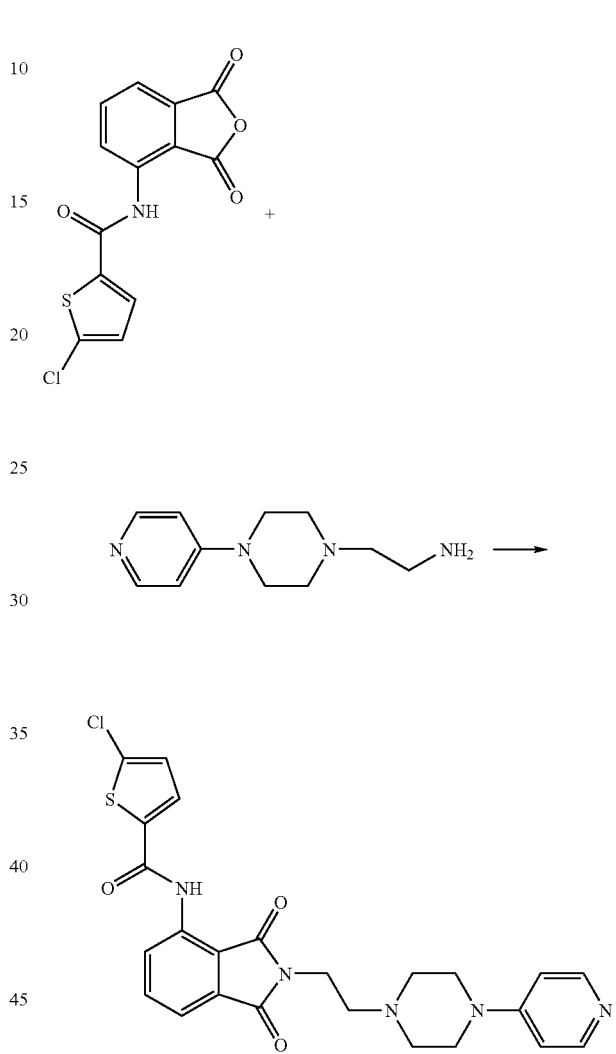

90 mg (0.2 mmol) of 5-chloro-N-{1,3-dioxo-2-[3-oxo-3-(1-piperazinyl)propyl]-2,3-dihydro-1H-isoindol-4-yl}-2-thiophenecarboxamide and 41 mg (0.4 mmol) of triethylamine are dissolved in 10 ml of THF, and 20.6 mg (0.2 mmol) of acetic anhydride are added. The reaction mixture is stirred at room temperature for 5 h, diluted with methylene chloride, washed with water, dried over magnesium sulfate, filtered and concentrated. This gives 81 mg (82% of theory) of the product.

MS=489 (M+H), RT (Method 6)=3.82 min.

Example 47

5-Chloro-N-(1,3-dioxo-2-{2-[4-(4-pyridinyl)piperazino]ethyl}-2,3-dihydro-1H-isoindol-4-yl)-2-thiophenecarboxamide 310 mg (1 mmol) of 5-chloro-N-(1,3-dioxo-1,3-dihydro-2-benzofuran-4-yl)-2-thiophenecarboxamide and 0.64 g (1 mmol) of 2-[4-(4-pyridinyl)piperazino]ethylamine (obtainable by heating 4-chloropyridine with aminoethylpiperazine or according to German Offenlegungsschrift 2024350) are boiled in 40 ml of glacial acetic acid overnight. 340 mg of 5-chloro-N-(1,3-dioxo-1,3-dihydro-2-benzofuran-4-yl)-2-thiophenecarboxamide are added and the mixture is then boiled for another 24 h and subsequently concentrated under reduced pressure, water is added, the aqueous phase is extracted four times with ethyl acetate and the combined organic phases are dried with Na$_2$SO$_4$, admixed with silica gel and concentrated under reduced pressure. Chromatography on silica gel using a toluene/ethyl acetate→toluene/ethanol gradient gives 140 mg (28.2% of theory) of the target compound of m.p. 168° C. and Rf (SiO$_2$, toluene/ethanol=1:1)=0.28.

Example 48

5-Chloro-N-{2-[2-(1-methyl-2-pyrrolidinyl)ethyl]-1,3-dioxo-2,3-dihydro-1H-isoindol-4-yl}-2-thiophenecarboxamide

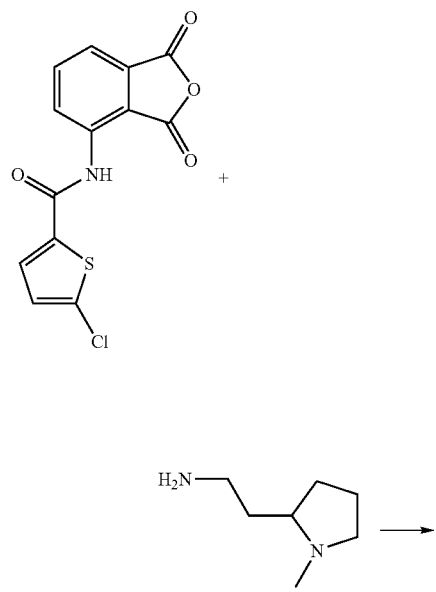

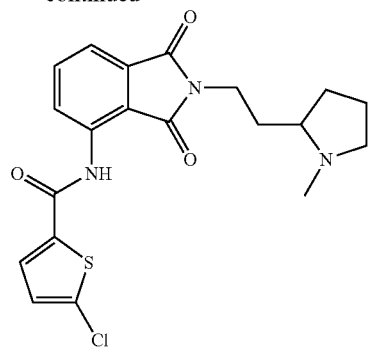

50 mg (0.16 mmol) of 5-chloro-N-(1,3-dioxo-1,3-dihydro-2-benzofuran-4-yl)-2-thiophenecarboxamide and 20.8 mg of (0.16 mmol) 2-(1-methyl-2-pyrrolidinyl)ethylamine are dissolved in 2 ml of dioxane and heated at reflux for 24 h. Removal of the solvent under reduced pressure gives 65 mg (97% of theory) of the desired product.

MS=418 (M+H); rt (Method 5)=2.36 min.

Alternatively, the reaction can also be carried out in the solvent acetic acid at reflux temperature. If required, the product can be purified by chromatography on silica gel ($CH_2Cl_2$/EtOH/conc. aqu. $NH_3$ solution mixtures).

The following compounds were obtained analogously by reacting the anhydride with the corresponding primary amines (2-[4-(2-pyrimidinyl)-1-piperazinyl]propylamine and 2-[4-(4-pyridinyl)-1-piperazinyl]propylamine can be prepared analogously to He, Woodruff, Brodbeck; *Bioorg. Med. Chem. Lett.* 1997; 7; 18; pp. 2399–2402):

| Example | Structure | MS (M + H) | LC retention time (Method) |
|---|---|---|---|
| 49 | 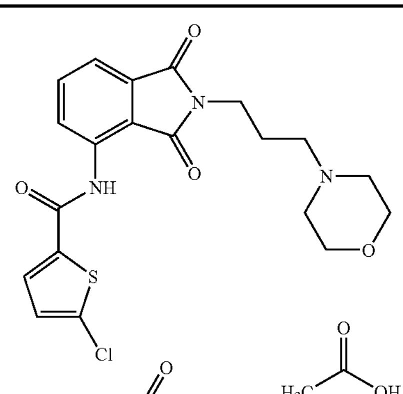 | 434 | 2.88 min (5) |
| 50 | 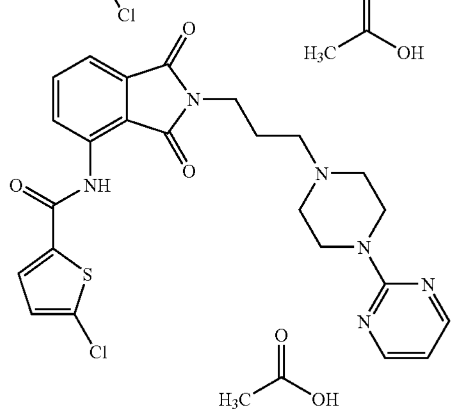 | 511 | 3.00 min (6) |

-continued
| Example | Structure | MS (M + H) | LC retention time (Method) |
|---|---|---|---|
| 51 | 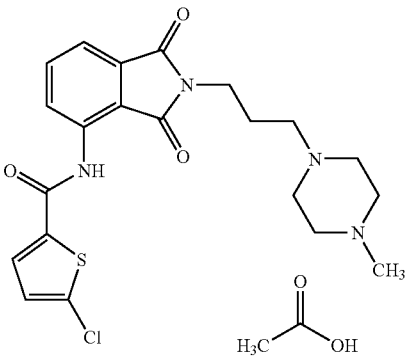 | 447 | 2.75 min (6) |
| 52 | 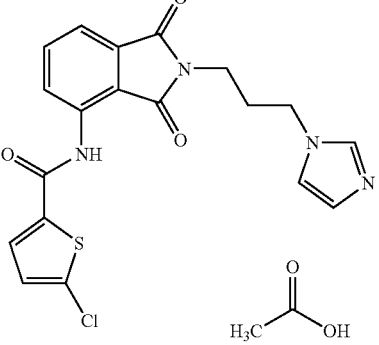 | 415 | 2.93 min (6) |
| 53 | 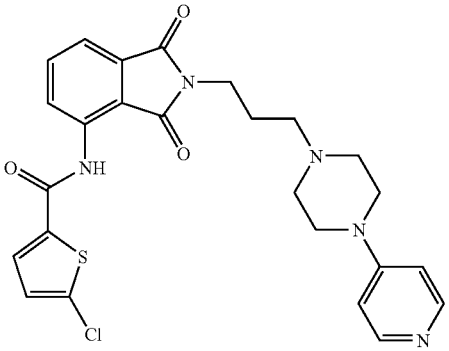 | 510 | 2.49 min (5) |

The following compounds were obtained analogously:

Example 54 tert-Butyl 4-(4-{[(5-chloro-2-thienyl)carbonyl]amino}-1,3-dioxo-1,3-dihydro-2H-isoindol-2-yl)butylcarbamate MS=478 (M+H), LC (Method 4): rt=5.74 min.

Example 55 tert-Butyl 6-(4-{[(5-chloro-2-thienyl)carbonyl]amino}-1,3-dioxo-1,3-dihydro-2H-isoindol-2-yl)hexylcarbamate MS=506 (M+H), LC (Method 4): rt=6.32 min.

Example 56

N-[2-(4-Aminobutyl)-1,3-dioxo-2,3-dihydro-1H-isoindol-4-yl]-5-chloro-2-thiophenecarboxamide trifluoroacetate

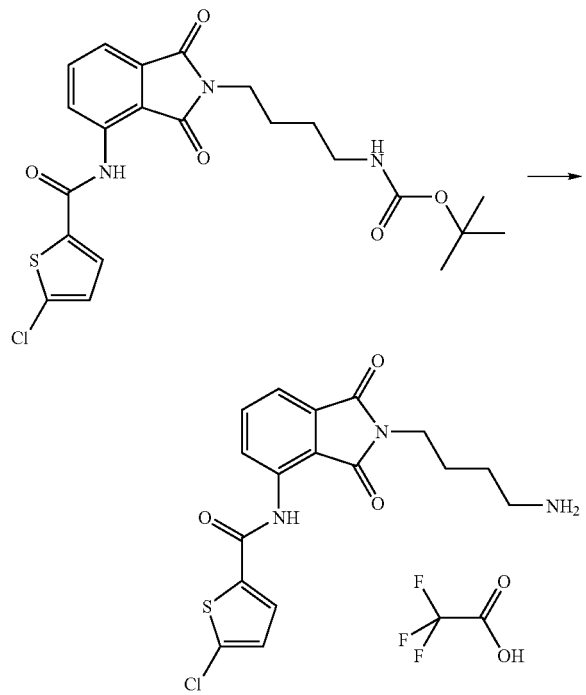

3.53 g (7.39 mmol) of tert-Butyl 4-(4-{[(5-chloro-2-thienyl)carbonyl]amino}-1,3-dioxo-1,3-dihydro-2H-isoindol-2-yl)butylcarbamate are dissolved in 150 ml of dichloromethane, and a solution of 10 ml of trifluoroacetic acid in 50 ml of dichloromethane is added at 0° C. The reaction mixture is slowly warmed to RT and stirred overnight. The reaction mixture is then concentrated and the oily residue is stored at 5° C. overnight. Dichloromethane and a little ethanol are added to the residue, which is now partially crystalline, and the mixture is filtered. This gives 3.44 g (95% of theory) of the desired product as a solid.

MS=378 (M+H), LC (Method 4): rt=3.01 min.

Example 57

N-[2-(6-Aminohexyl)-1,3-dioxo-2,3-dihydro-1H-isoindol-4-yl]-5-chloro-2-thiophenecarboxamide trifluoroacetate was obtained analogously by reacting tert-butyl-6-(4-{[(5-chloro-2-thienyl)carbonyl]amino}-1,3-dioxo-1,3-dihydro-2H-isoindol-2-yl)hexylcarbamate with trifluoroacetic acid.

MS=406 (M+H), LC (Method 4): rt=3.23 min.

Example 58

N-[4-(4-{[(5-Chloro-2-thienyl)carbonyl]amino}-1,3-dioxo-1,3-dihydro-2H-isoindol-2-yl)butyl]isonicotinamide

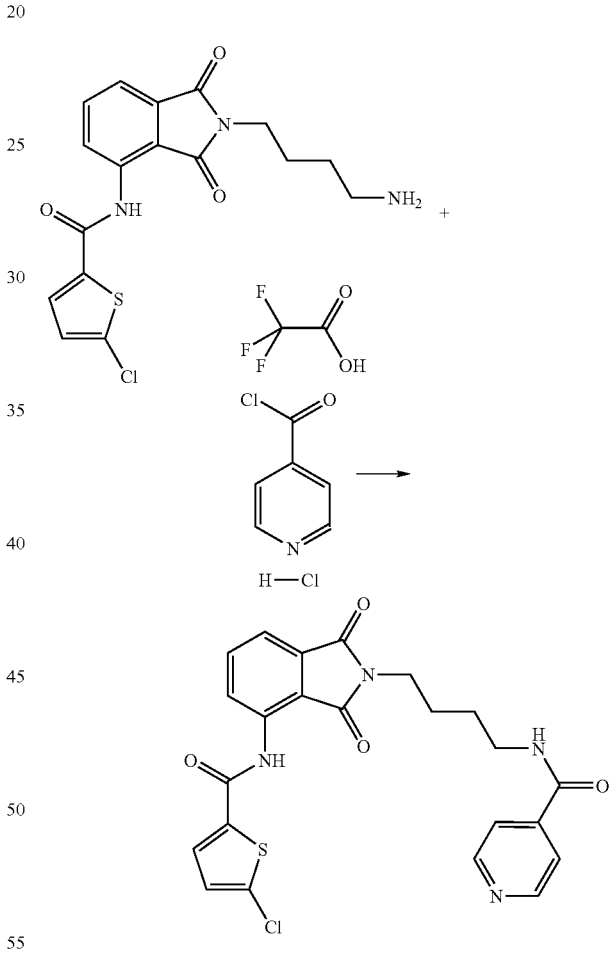

25 mg (0.24 mmol) of triethylamine and a catalytic amount of 4-dimethylaminopyridine are added to 40 mg (0.08 mmol) of N-[2-(4-aminobutyl)-1,3-dioxo-2,3-dihydro-1H-isoindol-4-yl]-5-chloro-2-thiophenecarboxamide trifluoroacetate in 2 ml of THF. At 0° C., 17.4 mg (0.10 mmol) of isonicotinoyl chloride hydrochloride are then added. The reaction mixture is warmed to RT, stirred at RT for 3 h and then heated at reflux for 20 h. After cooling to RT, the reaction mixture is diluted with dichloromethane and washed with aqu. sat. NaHCO₃ solution. The organic phase is dried over MgSO₄, filtered and concentrated. The crude product is chromatographed on silica gel ($CH_2Cl_2$/EtOH=50/1). This gives 18.5 mg (47% of theory) of the desired product.

MS=483 (M+H), LC (Method 4): rt=3.75 min.

Example 59 tert-Butyl 4-hydroxytetrahydro-1(2H)-pyridinecarboxylate

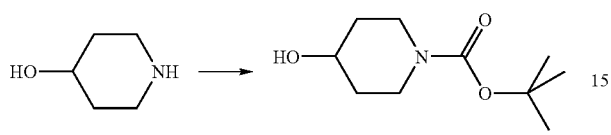

12.11 g (54.4 mmol) of di-tert-butyl dicarbonate (Boc anhydride) and 54.3 ml of 1N sodium hydroxide solution are added (over a period of 20 min) to an ice-cooled solution of 5 g (49.4 mmol) of 4-hydroxypiperidine in 50 ml of 1,4-dioxane. After 15 min, the ice-cooling is removed and the mixture is stirred at room temperature for 2 h. The mixture is concentrated and the aqueous phase, adjusted to a pH of about 6, is extracted with dichloromethane. The organic phase is dried over magnesium sulfate, concentrated and dried under high vacuum. Yield: 10.12 g (99% of theory); MS (DCI, $NH_4$): m/z (%)=202 (M+H, 82), 102 (100); LC-MS (Method 4): rt (%)=3.11 (100).

Example 60 tert-Butyl 4-(2-hydroxyethyl)tetrahydro-1(2H)-pyridinecarboxylate can be prepared in an analogous manner from 4-hydroxyethylpiperidine.

MS (DCI, $NH_4$): 230 (M+H, 70), 130 (100); HPLC (Method 2): rt (%)=3.72 (88).

Example 61

5-Chloro-N-(1,3-dioxo-2,3-dihydro-1H-isoindol-4-yl)-2-thiophenecarboxamide

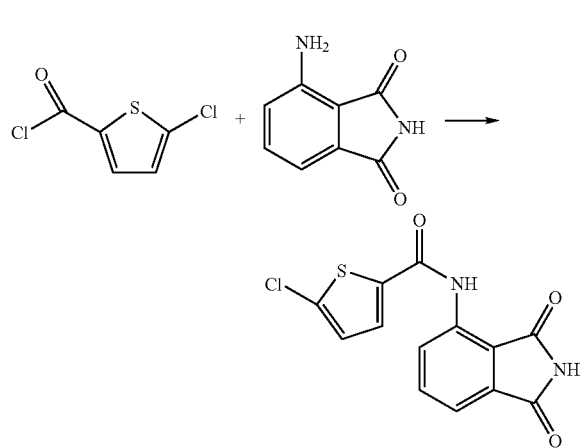

At 0° C., 7.8 g (43.7 mmol) of 3-aminophthalimide are dissolved with stirring in 200 ml of pyridine. 5-Chloro-2-thiophenecarbonyl chloride (obtained by boiling 5-chloro-2-thiophenecarboxylic acid in $SOCl_2$) is then added over a period of 5 min. The mixture is stirred at RT and monitored by TLC, the solution, initially clear, turning into a slurry. Another 200 ml of THF are added and the mixture is stirred at RT overnight.

The mixture is then poured into 500 ml of water and extracted with ethyl acetate. Relatively large amounts of poorly soluble crystals remain in the aqueous phase, these are filtered off with suction. The crystals are dissolved in 200 ml of THF and dried with $MgSO_4$. The solution is concentrated using a rotary evaporator and then once more triturated with ether and filtered off with suction. This gives 3.5 g (26.4% of theory) of the desired compound.

Example 62

5-Chloro-N-(1,3-dioxo-2-{[1-(4-pyridinyl)-4-piperidinyl]methyl}-2,3-dihydro-1H-isoindol-4-yl)-2-thiophenecarboxanmide

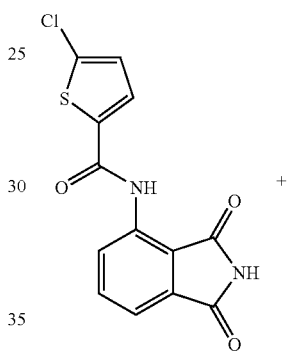

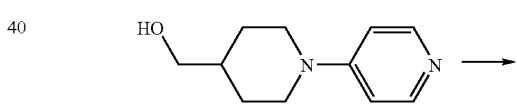

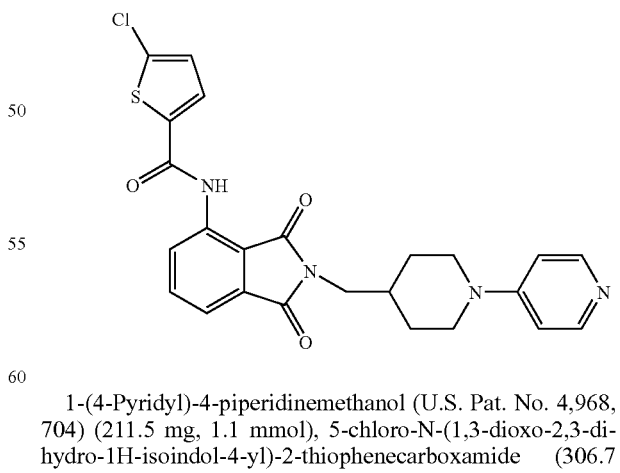

1-(4-Pyridyl)-4-piperidinemethanol (U.S. Pat. No. 4,968,704) (211.5 mg, 1.1 mmol), 5-chloro-N-(1,3-dioxo-2,3-dihydro-1H-isoindol-4-yl)-2-thiophenecarboxamide (306.7 mg, 1 mmol), triphenylphosphine (1049 mg, 4 mmol) are initially charged in 40 ml of THF, and diethylazodicarboxylate (DEAD) (696.6 mg, 4 mmol, 0.63 ml) is added. The mixture is stirred at room temperature overnight and then concentrated by evaporation, the residue is dissolved in ethanol, silica gel is added, the mixture is re-concentrated by evaporation and the residue is applied to a silica gel column. Elution with toluene/ethyl acetate and toluene/ethanol (25:1) mixtures gives a main fraction of Rf (SiO$_2$, toluene/ethanol=4:1)=0.19. This fraction is evaporated and treated with ethanol, and the resulting crystals (112 mg, 23.3% of theory) are filtered off with suction. M.p.: 123° C. (decomp.).

The following compound is obtained analogously:

Example 63

5-Chloro-N-{1,3-dioxo-2-[1-(4-pyridinyl)-4-piperidinyl]-2,3-dihydro-1H-isoindol-4-yl}-2-thiophenecarboxaimide M.p. 214° C., Rf (SiO$_2$, toluene-ethanol 1:1): 0.4.

Example 64

5-Chloro-N-[1,3-dioxo-2-(4-piperidinylmethyl)-2,3-dihydro-1H-isoindol-4-yl]-2-thiophenecarboxamide

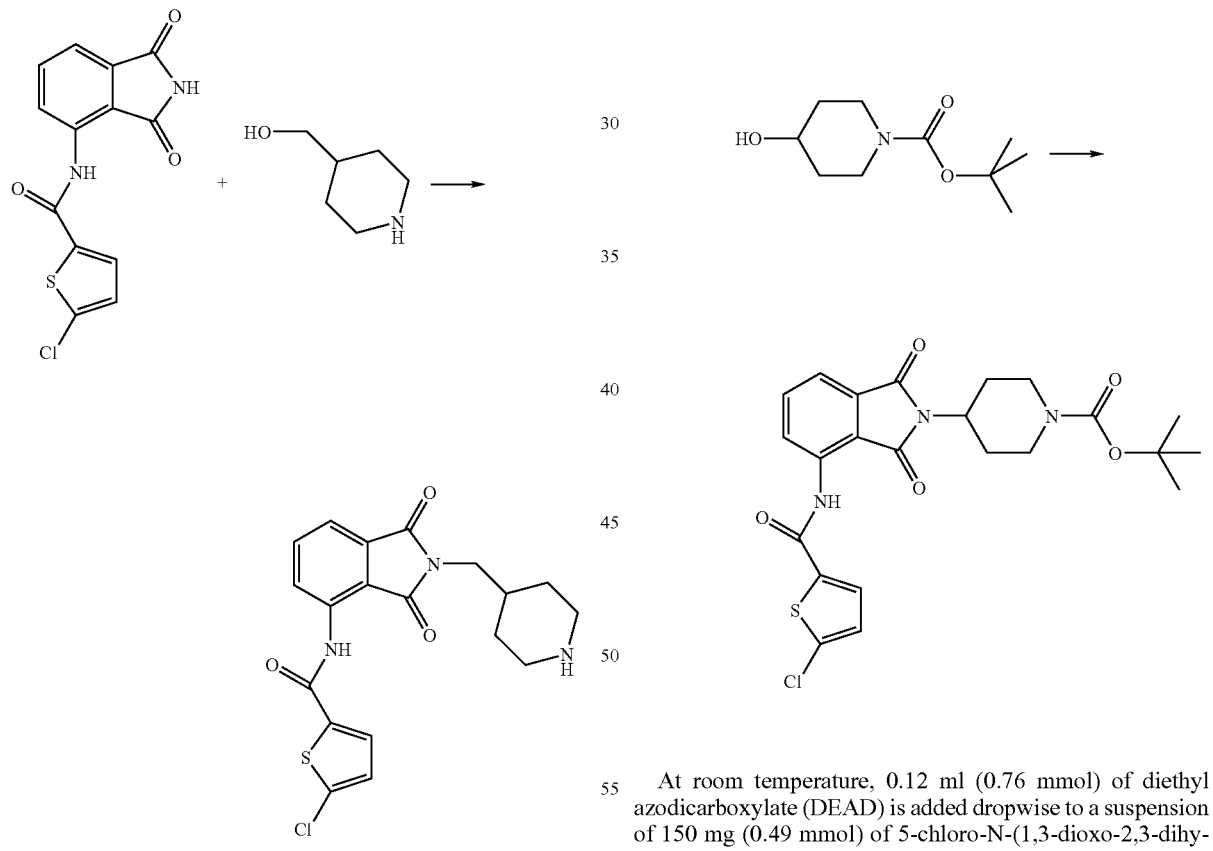

At room temperature, 0.43 ml (2.73 mmol) of diethyl azodicarboxylate (DEAD) is added dropwise to a suspension of 670 mg (2.18 mmol) of 5-chloro-N-(1,3-dioxo-2,3-dihydro-1H-isoindol-4-yl)-2-thiophenecarboxamide, 314 mg (2.73 mmol) of 4-hydroxymethylpiperidine and 716 mg (2.73 mmol) of triphenylphosphine in 8.7 ml of absolute THF. After 2 h at room temperature, the mixture is concentrated and the residue is separated by chromatography on silica gel (gradient: from dichloromethane/methanol 95:5 to dichloromethane/methanol/triethylamine 9:1:0.1). Yield: 430 mg (41.5% of theory); MS (ESI): m/z (%)=404 (M+H, 60), 145 (100); LC-MS (Method 4): rt (%)=3.02 (84).

Example 65 tert-Butyl 4-(4-{[(5-chloro-2-thienyl)carbonyl]amino}-1,3-dioxo-1,3-dihydro-2H-isoindol-2-yl)tetrahydro-1(2H)-pyridinecarboxylate

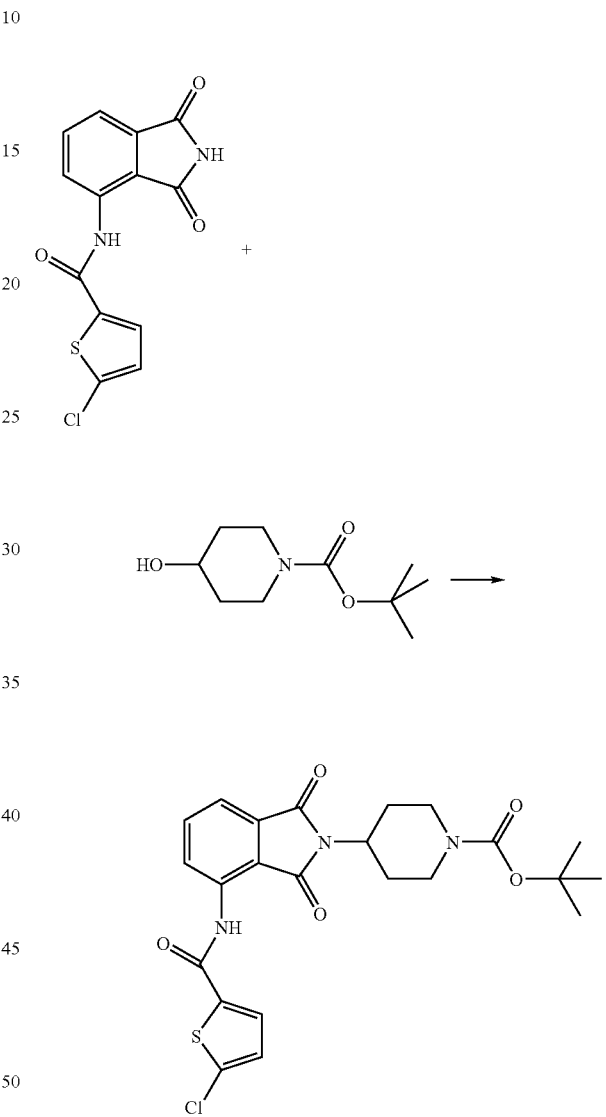

At room temperature, 0.12 ml (0.76 mmol) of diethyl azodicarboxylate (DEAD) is added dropwise to a suspension of 150 mg (0.49 mmol) of 5-chloro-N-(1,3-dioxo-2,3-dihydro-1H-isoindol-4-yl)-2-thiophenecarboxamide, 148 mg (0.73 mmol) of tert-butyl 4-hydroxytetrahydro-1(2H)-pyridinecarboxylate and 199 mg (0.76 mmol) of triphenylphosphine in 1.95 ml of absolute THF. After 2 h at room temperature, the mixture is concentrated and the residue is separated by chromatography on silica gel (dichloromethane/methanol mixture) and the product is isolated.

Yield: 184 mg (76.8% of theory); MS (LC-MS): m/z (%)=279 (M+H, 100); LC-MS (Method 4): rt (%)=3.88 (98.9).

Example 66

5-Chloro-N-[1,3-dioxo-2-(4-piperidinyl)-2,3-dihydro-1H-isoindol-4-yl]-2-thiophenecarboxamide

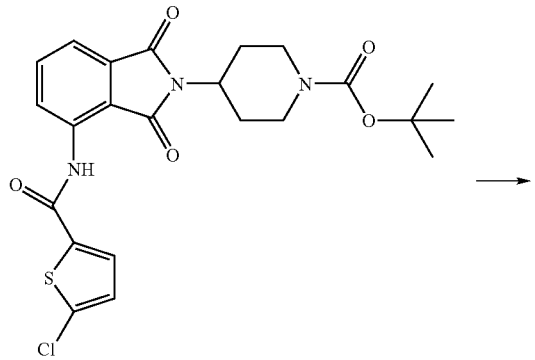

50 ml of a mixture of TFA and water (9:1) are added dropwise to an ice-cooled mixture of 1.82 g (3.71 mmol) of tert-butyl 4-(4-{[(5-chloro-2-thienyl)carbonyl]-amino}-1,3-dioxo-1,3-dihydro-2H-isoindol-2-yl)tetrahydro-1(2H)-pyridine-carboxylate in 50 ml of chloroform. The ice-cooling is removed and the mixture is stirred at room temperature for 1.5 h and then concentrated. The residue is taken up in dichloromethane/methanol and washed with sat. sodium bicarbonate solution, dried over magnesium sulfate and concentrated. The crude product can be purified further by crystallization with ether. Yield: 1.185 g (78% of theory); MS (DCI, NH$_4$): m/z (%)=390 (M+H, 100).

Example 67

In an analogous manner, 5-chloro-N-{1,3-dioxo-2-[2-(4-piperidinyl)ethyl]-2,3-dihydro-1H-isoindol-4-yl}-2-thiophenecarboxamide was obtained from tert-butyl 4-[2-(4-{[(5-chloro-2-thienyl)carbonyl]amino}-1,3-dioxo-1,3-dihydro-2H-isoindol-2-yl)ethyl]tetrahydro-1(2H})-pyridinecarboxylate.

MS (ESI): m/z (%)=418 (M+H, 100); HPLC (Method 1): rt (%)=3.82 (78).

Example 68

5-Chloro-N-{2-[1-(cyanomethyl)-4-piperidinyl]-1,3-dioxo-2,3-dihydro-1H-isoindol-4-yl}-2-thiophenecarboxamide

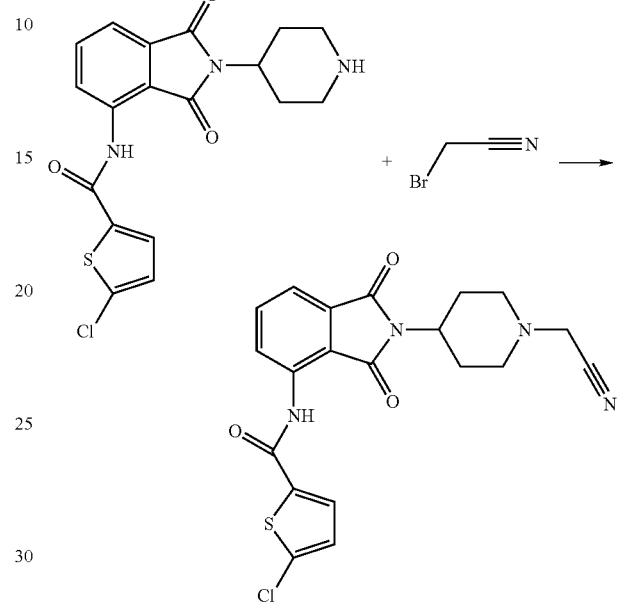

A mixture of 100 mg (0.26 mmol) of 5-chloro-N-[1,3-dioxo-2-(4-piperidinyl)-2,3-dihydro-1H-isoindol-4-yl]-2-thiophenecarboxamide, 0.022 ml (0.31 mmol) of α-bromoacetonitrile and 0.072 ml (0.51 mmol) of triethylamine in 2.5 ml of DMF are stirred at room temperature overnight. The mixture is concentrated and the residue is taken up in dichloromethane, washed with sodium bicarbonate solution, dried over magnesium sulfate and concentrated. The product is crystallized with ether, filtered off with suction and dried under high vacuum. Alternatively, the product can be purified by chromatography on silica gel (dichloromethane/methanol mixtures).

Yield: 92.2 mg (83.8% of theory); MS (DCI, NH$_4$): m/z (%)=429 (M+H, 100); HPLC (Method 1): rt (%)=4.51 (100).

The following compounds can be prepared in an analogous manner from the corresponding amine derivatives and α-bromoacetonitrile:

Example 69

5-Chloro-N-(2-{[1-(cyanomethyl)-4-piperidinyl]methyl}-1,3-dioxo-2,3-dihydro-1H-isoindol-4-yl)-2-thiophenecarboxamide MS (ESI): m/z (%)=443 (M+H, 12), 416 (100); HPLC (Method 1): rt (%)=4.41 (97).

Example 70

5-Chloro-N-(2-{2-[1-(cyanomethyl)-4-piperidinyl]ethyl}-1,3-dioxo-2,3-dihydro-1H-isoindol-4-yl)-2-thiophenecarboxamide MS (DCI, NH$_4$): m/z (%)=457 (M+H, 100); HPLC (Method 1): rt (%)=4.49 (95).

Example 71

4-[2-(4-{[(5-Chloro-2-thienyl)carbonyl]amino}-1,3-dioxo-1,3-dihydro-2H-isoindol-2-yl)ethyl]-1,1-dimethylpiperidinium iodide

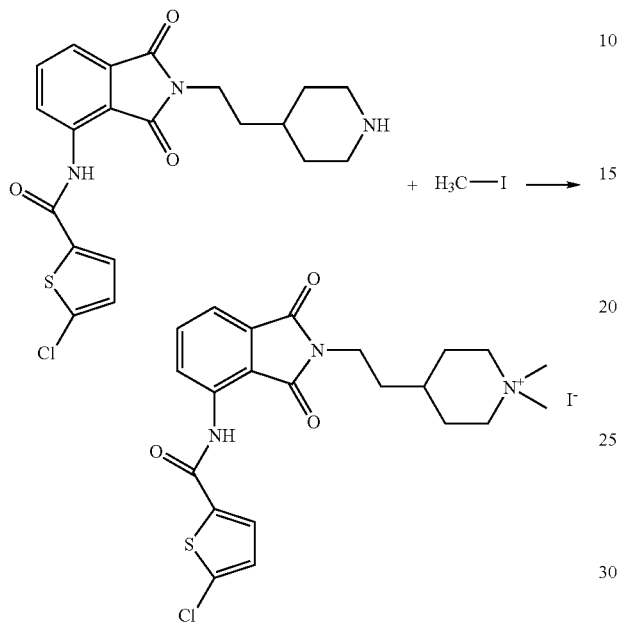

50 mg (0.12 mmol) of 5-chloro-N-{1,3-dioxo-2-[2-(4-piperidinyl)ethyl]-2,3-dihydro-1H-isoindol-4-yl}-2-thiophenecarboxamide are dissolved in 2 ml of 1,2-dichloroethane, 0.025 ml of N,N-diisopropylethylamine are added and the mixture is treated with excess methyl iodide. The mixture is stirred at room temperature overnight. Water and dichloromethane are added to the residue. The insoluble solid is filtered off and dried under high vacuum.

Yield: 51.5 mg (74.8% of theory); LC-MS (Method 1): rt (%)=3.02 (84), m/z (%)=446 ($M^+$–I, 100).

Example 72

5-Chloro-N-{2-[2-(1-ethyl-4-piperidinyl)ethyl]-1,3-dioxo-2,3-dihydro-1H-isoindol-4-yl}-2-thiophenecarboxamide

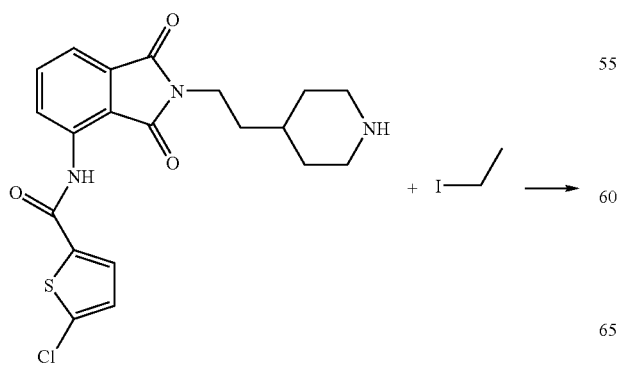

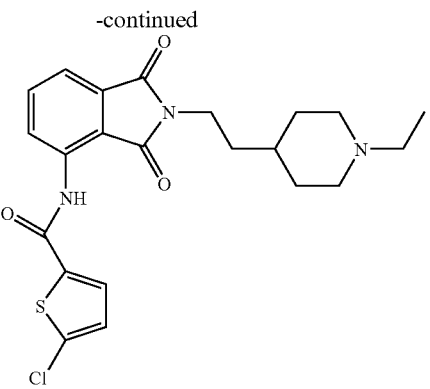

50.1 mg (0.12 mmol) of 5-chloro-N-{1,3-dioxo-2-[2-(4-piperidinyl)ethyl]-2,3-dihydro-1H-isoindol-4-yl}-2-thiophenecarboxamide are dissolved in 1 ml of 1,4-dioxane, and 25 µl (0.144 mmol) of N,N-diisopropylethylamine and 10 µl (0.12 mmol) of iodoethane are added. The mixture is stirred at room temperature overnight and, after concentration, chromatographed on silica gel (dichloromethane/methanol 97:3).

Yield: 5.6 mg (10.5% of theory); LC-MS (Method 1): rt (%)=3.09 (95); m/z (%)=446 (M+H, 100).

Example 73

N-{2-[2-(1-Acetyl-4-piperidinyl)ethyl]-1,3-dioxo-2,3-dihydro-1H-isoindol-4-yl}-5-chloro-2-thiophenecarboxamide

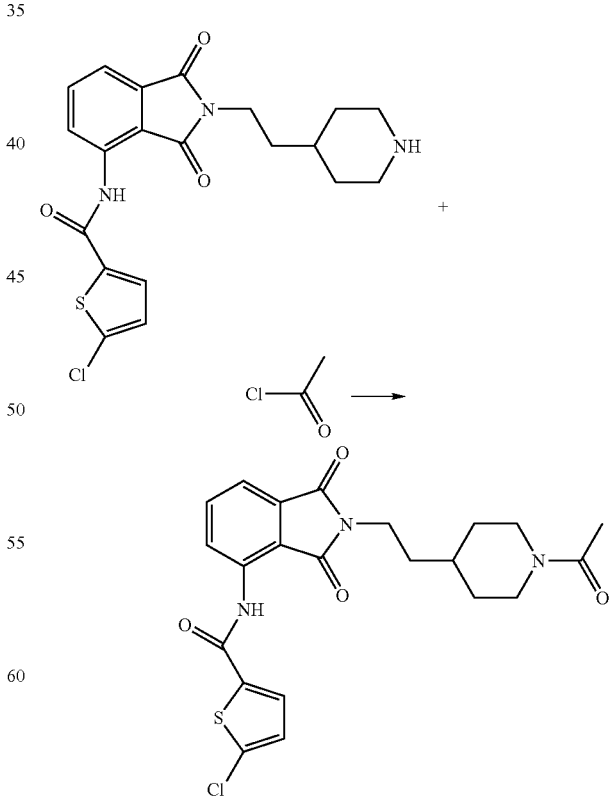

At room temperature, 17 µl (0.24 mmol) of acetyl chloride are added dropwise to a solution of 50 mg (0.12 mmol) of 5-chloro-N-{1,3-dioxo-2-[2-(4-piperidinyl)ethyl]-2,3-dihydro-1H-isoindol-4-yl}-2-thiophenecarboxamide and 0.1 ml of pyridine in 1 ml of absolute dichloromethane. After 1 h at room temperature, a few drops of water are added and the mixture is diluted with dichloromethane. The mixture is washed with saturated sodium bicarbonate solution, dried over magnesium sulfate and concentrated. The crude product is purified by chromatography on silica gel (dichloromethane/methanol 98:2).

Yield: 41.8 mg (76% of theory); MS (ESI): m/z (%)=482 (M+Na, 18), 460 (M+H, 45); HPLC (Method 1): rt (%)=4.92 (94).

Example 74

4-[2-(4-{[(5-Chloro-2-thienyl)carbonyl]amino}-1,3-dioxo-1,3-dihydro-2H-isoindol-2-yl)ethyl]-1-piperidinecarboxamide

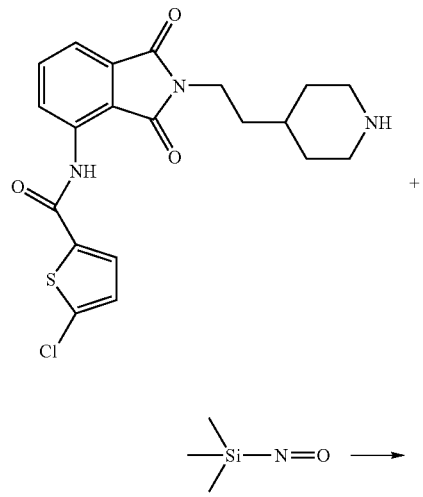

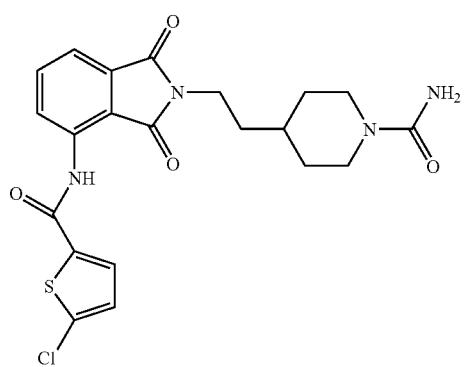

At room temperature, 0.18 ml of trimethylsilyl isocyanate are added dropwise to a suspension of 50 mg (0.12 mmol) of 5-chloro-N-{1,3-dioxo-2-[2-(4-piperidinyl)ethyl]-2,3-dihydro-1H-isoindol-4-yl}-2-thiophenecarboxamide in 2.5 ml of absolute dichloromethane. The mixture is stirred at room temperature for 48 h and then, after concentration, chromatographed on silica gel (dichloromethane/methanol 97:3).

Yield: 31.1 mg (56.4% of theory); MS (ESI): m/z (%)=483 (M+Na, 8), 461 (M+H, 15), 444 (45); HPLC (Method 1): rt (%)=4.60 (85).

Example 75

5-Chloro-N-{1,3-dioxo-2-[1-(2-pyridinyl)-4-piperidinyl]-2,3-dihydro-1H-isoindol-4-yl}-2-thiophenecarboxamide

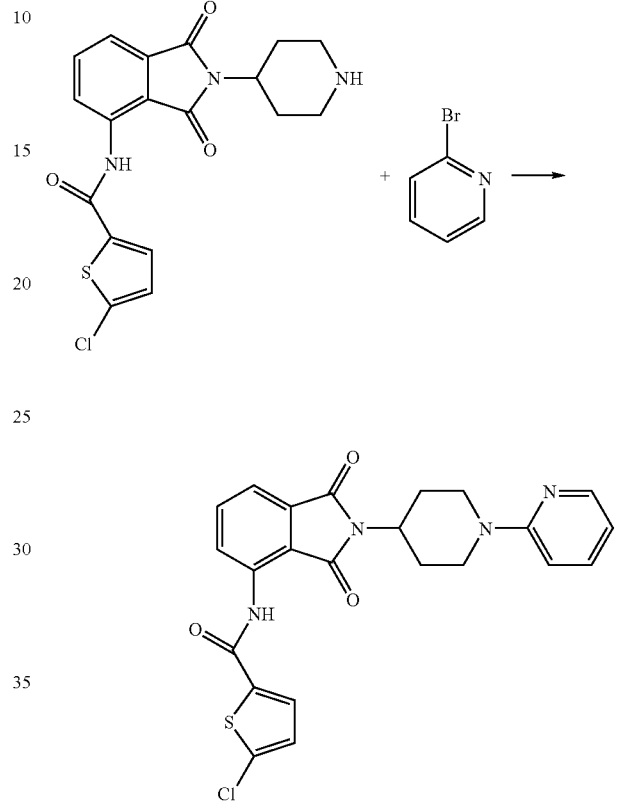

100 mg (0.257 mmol) of 5-chloro-N-[1,3-dioxo-2-(4-piperidinyl)-2,3-dihydro-1H-isoindol-4-yl]-2-thiophenecarboxamide and 0.05 ml (0.513 mmol) of 2-bromopyridine in 0.5 ml of pyridine are stirred at 110° C. for 48 h. The mixture is concentrated and dried under high vacuum. The product is isolated by preparative RP-HPLC.

Yield: 15 mg (12.5% of theory); MS (DCI, NH$_4$): M/Z (%)=467 (M+H, 100); HPLC (Method 1): rt (%)=4.6 (100).

Example 76

In analogous manner, 5-chloro-N-(1,3-dioxo-2-{2-[1-(2-pyridinyl)-4-piperidinyl]ethyl}-2,3-dihydro-1H-isoindol-4-yl)-2-thiophenecarboxamide can be prepared from 5-chloro-N-{1,3-dioxo-2-[2-(4-piperidinyl)ethyl]-2,3-dihydro-1H-isoindol-4-yl}-2-thiophenecarboxamide and 2-bromopyridine MS (ESI): m/z (%)=914 (M+H, 15); HPLC (Method 1): rt (%)=4.79 (93).

Example 77 tert-Butyl 4-[2-(4-nitro-1-oxo-1,3-dihydro-2H-isoindol-2-yl)ethyl]-1-piperidinecarboxylate

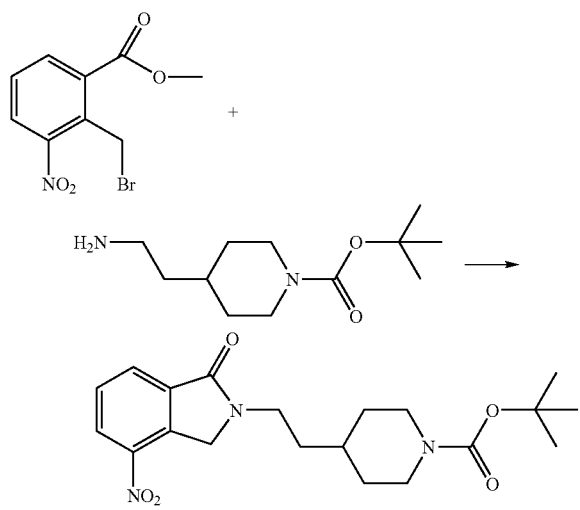

2.7 g (9.81 mmol) of methyl 2-(bromomethyl)-3-nitrobenzoate (*J. Org. Chem.*, 1999, 9731–9734) and 2.25 g (9.81 mmol) of tert-butyl 4-(2-aminoethyl)-1-piperidinecarboxylate (*J. Med. Chem.*, 1997, 1779–1788) are dissolved in 45 ml of absolute DMF, 2.05 ml of triethylamine are added and the mixture is stirred at 70° C. for 2 h. After cooling, water is added to the reaction mixture. The organic phase is taken up in dichloromethane, dried over magnesium sulfate and concentrated. The crude product is purified by chromatography on silica gel.

Yield: 1.96 g (51.3% of theory); MS (DCI, $NH_4$): m/z (%)=390 (M+H, 10), 290 (100); HPLC (Method 2): rt (%)=4.57 (100).

Example 78 tert-Butyl 4-[2-(4-amino-1-oxo-1,3-dihydro-2H-isoindol-2-yl)ethyl]-1-piperidinecarboxylate

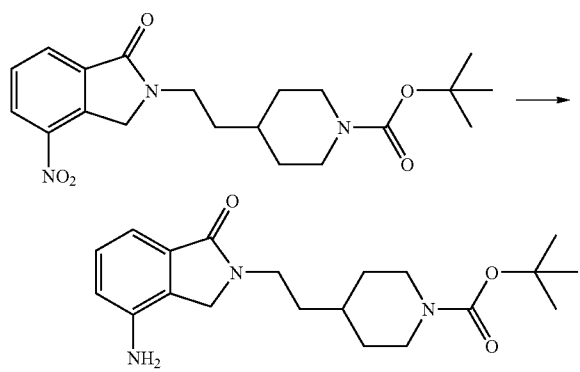

450 mg of Pd/C (10%) are added to a mixture of 2.1 g (5.4 mmol) of tert-butyl 4-[2-(4-nitro-1-oxo-1,3-dihydro-2H-isoindol-2-yl)ethyl]-1-piperidinecarboxylate in 25 ml of methanol. The mixture is stirred at atmospheric pressure under an atmosphere of hydrogen for 2 h and, after filtration through Celite, concentrated. The product is purified by column filtration on silica gel (dichloromethane/methanol 9:1).

Yield: 1.72 g (88.7% of theory); MS (DCI, $NH_4$): m/z (%)=377 (M+$NH_4$, 100); HPLC (Method 1): rt (%)=3.79 (100).

Example 79 tert-Butyl 4-[2-(4-{[(5-chloro-2-thienyl)carbonyl]amino}-1-oxo-1,3-dihydro-2H-isoindol-2-yl)ethyl]-1-piperidinecarboxylate

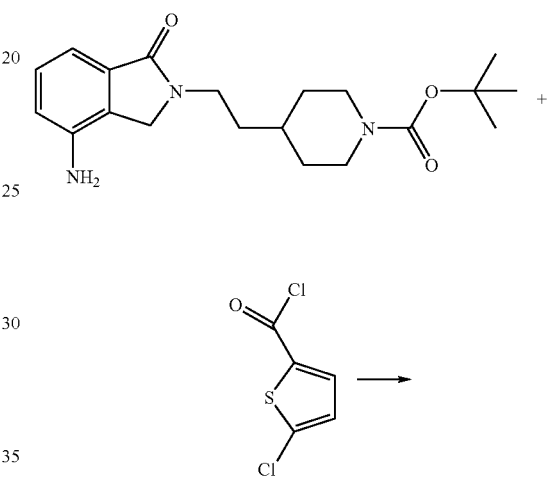

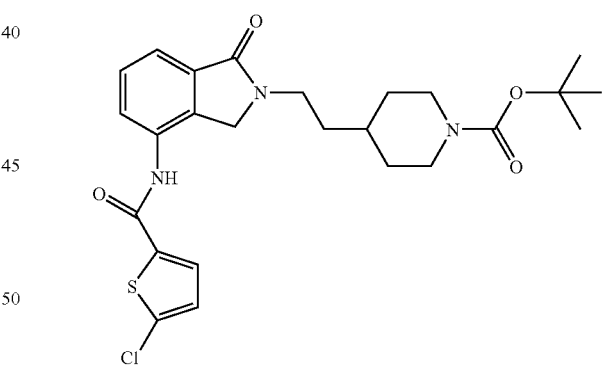

At 0° C., 0.97 g (5.35 mmol) of 5-chlorothiophene-2-carbonyl chloride is added dropwise to a suspension of 1.48 g (4.12 mmol) of tert-butyl 4-[2-(4-amino-1-oxo-1,3-dihydro-2H-isoindol-2-yl)ethyl]-1-piperidinecarboxylate, 1.7 ml (20.6 mmol) of pyridine and 25 mg (0.206 mmol) of 4-DMAP in 21 ml of absolute THF. The mixture is slowly warmed to room temperature and stirred overnight. The reaction 10 mixture is concentrated and then separated by chromatography on silica gel (dichloromethane/methanol 97:3).

Yield: 1.95 g (94% of theory); MS (ESI): m/z (%)=504 (M+H, 15), 447 (28), 404 (100); HPLC (Method 3): rt (%)=4.98 (95).

Example 80

5-Chloro-N-(1-oxo-2-{2-oxo-2-[4-(4-pyridinyl)piperazino]ethyl}-2,3-dihydro-1H-isoindol-4-yl)-2-thiophenecarboxamide and of 5-chloro-N-(3-oxo-2-{2-oxo-2-[4-(4-pyridinyl)piperazino]ethyl}-2,3-dihydro-1H-isoindol-4-yl)-2-thiophenecarboxamide

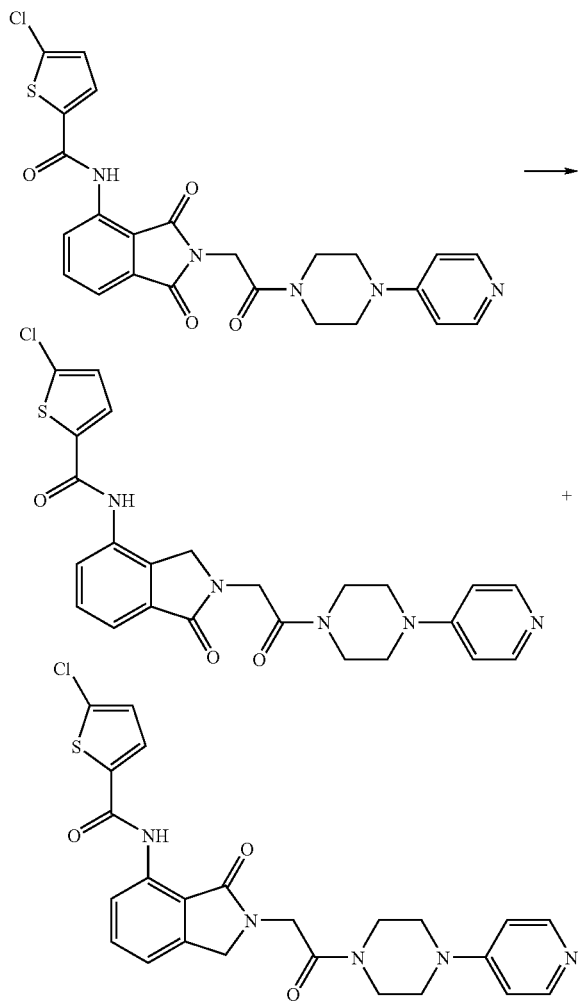

134 mg (3.53 mmol) of sodium borohydride are added to a solution of 1.5 g (2.94 mmol) of 5-chloro-N-(1,3-dioxo-2-{2-oxo-2-[4-(4-pyridinyl)piperazino]ethyl}-2,3-dihydro-1H-isoindol-4-yl)-2-thiophenecarboxamide in 60 ml of methanol, and the mixture is stirred at room temperature for 2 hours. The resulting solution of 5-chloro-N-(3-hydroxy-2-{2-oxo-2-[4-(4-pyridinyl)piperazino]ethyl}-2,3-dihydro-1H-isoindol-4-yl)-2-thiophenecarboxamide [$^1$H NMR: 3.6–3.9 (m, 8H), 4.22 (d, 1H), 4.68 (d, 1H), 6.12 (s, 1H), 7.2 (d, 2H), 7.3 (d, 1H), 7.55 (d, 1H), 7.6 (t, 1H), 7.7 (d, 1H), 7.88 (d, 1H), 8.28 (d, 2H), 10.3 (s, 1H), 13.5 (s, 1H)] and 5-chloro-N-(1-hydroxy-2-{2-oxo-2-[4-(4-pyridinyl)piperazino]ethyl}-2,3-dihydro-1H-isoindol-4-yl)-2-thiophenecarboxamide [$^1$H NMR: 3.6–3.9 (m, 8H), 4.22 (d, 1H), 4.7 (d, 1H), 5.85 (s, 1H), 7.2 (d, 2H), 7.38 (d, 1H), 7.61 (d, 1H), 7.68 (t, 1H), 7.63 (t, 1H), 8.25–8.32 (m, 3H), 11.0 (s, 1H), 13.41 (s, 1H)] is admixed with 2N HCl and extracted with methylene chloride. The organic phase is concentrated under reduced pressure (0.35 g) and the crystals which are insoluble in the aqueous and organic phase are filtered off with suction (0.5 g). 1.336 g of trifluoroacetic acid and then 0.341 g (2.93 mmol) of triethylsilane are added to 0.5 g of this mixture in 10 ml of methylene chloride, and the mixture is stirred at room temperature overnight. The mixture is then evaporated to dryness under reduced pressure and the residue is chromatographed on RP8 silica gel using a 4:1 to 1:1 mixture of water and acetonitrile.

The two isomers are obtained, the compound eluting first being the trifluoroacetate of the 1-oxo isomer: $^1$H NMR(400 MHz, d$^6$-DMSO): δ=3.6–3.9 (m, 8H), 4.50 (s, 2H), 4.55 (s, 2H), 7.21 (d, 2H), 7.30 (d, 1H), 7.50–7.70 (m, 3H), 7.90 (d, 1H), 8.30 (d, 2H), 10.52 (s, 1H), 13.50 (broad s, 1H).

3-Oxo isomer (trifluoroacetate): $^1$H NMR(400 MHz, d$^6$-DMSO): δ=3.6–3.9 (m, 8H), 4.57 (s, 2H), 4.59 (s, 2H), 7.21 (d, 2H), 7.31 (m, 2H), 7.6 (d, 1H), 7.63 (t, 1H), 8.28 (d, 1H), 8.3 (d, 2H), 11.23 (s, 1H), 13.58 (broad s, 1H).

Analogously, 5-chloro-N-(1,3-dioxo-2-{2-[4-(4-pyridinyl)piperazino]ethyl}-2,3-dihydro-1H-isoindol-4-yl)-2-thiophenecarboxamide gives, by reduction with NaBH$_4$ and, if appropriate, subsequent reduction with triethylsilane/TFA, the TFA salts of the following compounds, where triethylsilane was added first, followed by TFA:

| Example | Structure | MS |
|---|---|---|
| 81 | (5-chlorothiophene-carboxamide-1-hydroxy-isoindolinone-ethylpiperazinyl-pyridine structure) | 498 (M + H) |

-continued

| Example | Structure | MS |
|---|---|---|
| 82 | 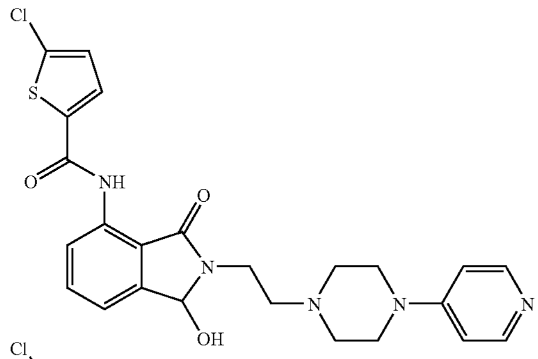 | 498 (M + H) |
| 83 | 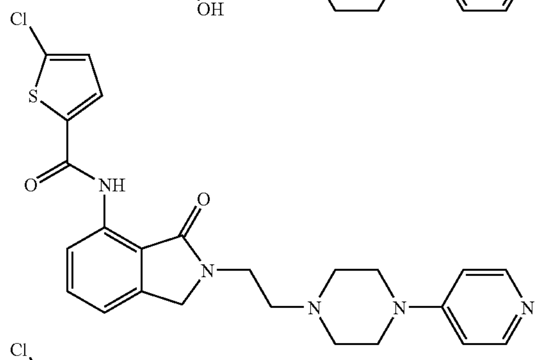 | 482 (M + H) |
| 84 | 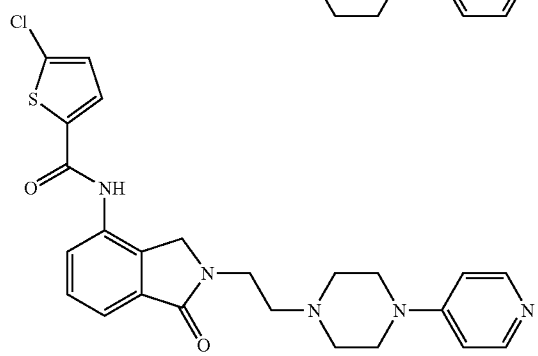 | 482 (M + H) |

Analogously, 5-chloro-N-(1,3-dioxo-2-{3-oxo-3-[4-(4-pyridinyl)piperazino]propyl}-2,3-dihydro-1H-isoindol-4-yl)-2-thiophenecarboxamide gives, by reduction with NaBH$_4$ and, if appropriate, subsequent reduction with triethylsilane/TFA, the TFA salts of the following compounds, where triethylsilane was added first, followed by TFA:

| Example | Structure | $^1$H NMR or melting point |
|---|---|---|
| 85 | 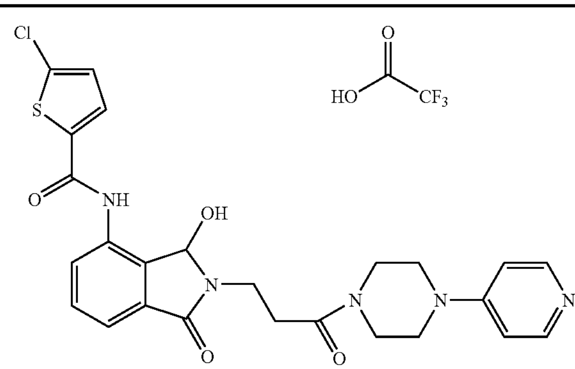 | 2.65–2.8 (m, 1H), 2.8–2.9 (m, 1H), 3.55–3.8 (m, 10H), 6.1 (s, 1H), 7.18 (d, 2H), 7.3 (d, 1H), 7.5 (d, 1H), 7.55 (t, 1H), 7.68 (d, 1H), 7.88 (d, 1H), 8.3 (d, 2H), 10.31 (s, 1H), 13.49 (s, 1H) |

-continued

| Example | Structure | ¹H NMR or melting point |
|---------|-----------|------------------------|
| 86 | 5-chlorothiophene-carboxamide linked to 3-oxo-1-hydroxy-isoindoline N-CH₂CH₂-C(O)-piperazine-pyridin-4-yl; HO-C(O)-CF₃ | 2.6–2.75 (m, 1H), 2.75–2.95 (m, 1H), 3.6–3.8 (m, 10H), 5.95 (s,1H), 7.18 (d, 2H), 7.31 (d, 1H), 7.32 (d, 1H), 7.62 (d, 1H), 7.63 (t, 1H), 8.25 (d, 1H), 8.26 (d, 2H), 11.05 (s, 1H), 13.42 (s, 1H) |
| 87 | 5-chlorothiophene-carboxamide linked to 3-oxo-isoindoline N-CH₂CH₂-C(O)-piperazine-pyridin-4-yl; HO-C(O)-CF₃ | 2.7–2.85 (m, 2H), 3.55–3.85 (m, 10H), 4.5 (s, 2H), 7.2 (d, 2H), 7.3 (d, 1H), 7.5–7.65 (m, 3H), 7.9 (d, 1H), 8.3 (d, 2H), 10.6 (s, 1H), 13.55 (s, 1H) |
| 88 | 5-chlorothiophene-carboxamide linked to 3-oxo-isoindoline N-CH₂CH₂-C(O)-piperazine-pyridin-4-yl | m.p. 118° C. |

Reduction of 5-chloro-N-(2-{2-[4-(hydroxymethyl)piperidino]-2-oxoethyl}-1,3-dioxo-2,3-dihydro-1H-isoindol-4-yl)-2-thiophenecarboxamide with NaBH₄ and, if appropriate, subsequently with triethylsilane/TFA gives the following compounds:

| Example | Structure | Melting point or Rf value |
|---------|-----------|---------------------------|
| 89 | 5-chlorothiophene-carboxamide linked to 1-oxo-3-hydroxy-isoindoline N-CH₂-C(O)-[4-(hydroxymethyl)piperidine] | m.p. 233° C. |

-continued

| Example | Structure | Melting point or Rf value |
|---|---|---|
| 90 | 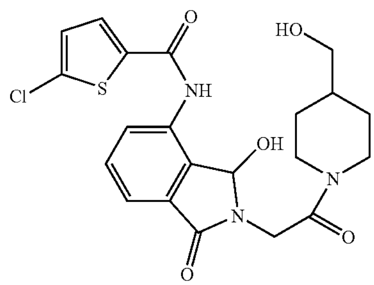 | m.p. 234° C. (decomp.) |
| 91 | 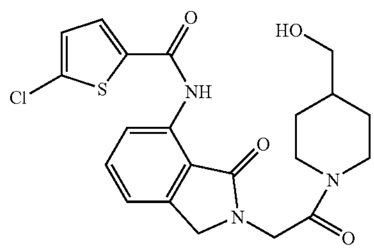 | Rf = 0.43 (SiO$_2$, Tol/EtOH 4/1) |
| 92 | 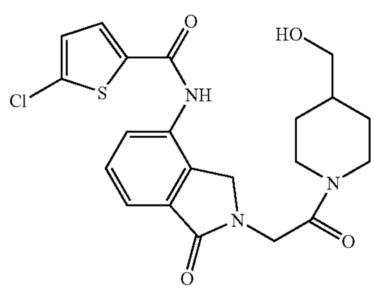 | m.p. 209° C.; Rf = 0.34 (SiO$_2$, Tol/EtOH 4/1) |

Reduction of 5-chloro-N-(1,3-dioxo-2-{[1-(4-pyridinyl)-4-piperidinyl]methyl}-2,3-dihydro-1H-isoindol-4-yl)-2-thiophenecarboxamide with NaBH$_4$ and, if appropriate, subsequently with triethylsilane/TFA gives the following compounds:

| Example | Structure | MS/Rf value |
|---|---|---|
| 93 | TFA salt | MS: 467 (M + H) |

-continued

| Example | Structure | MS/Rf value |
|---|---|---|
| 94 | (5-chloro-thiophene-2-carboxamide linked to 3-oxo-1-hydroxy-isoindoline with N-CH2-piperidine-N-pyridin-4-yl); TFA salt | Rf = 0.23 (SiO$_2$, Tol/EtOH 1/1) |
| 95 | (5-chloro-thiophene-2-carboxamide linked to 1-hydroxy-3-oxo-isoindoline with N-CH2-piperidine-N-pyridin-4-yl); TFA salt | Rf = 0.23 (SiO$_2$, Tol/EtOH 1/1) |
| 96 | (5-chloro-thiophene-2-carboxamide linked to 3-oxo-isoindoline with N-CH2-piperidine-N-pyridin-4-yl) | MS: 467 (M + H) |

Example 97

5-Chloro-N-{3-oxo-2-[3-oxo-3-(1-piperazinyl)propyl]-2,3-dihydro-1H-isoindol-4-yl}-2-thiophenecarboxamide and 5-chloro-N-{1-oxo-2-[3-oxo-3-(1-piperazinyl)-propyl]-2,3-dihydro-1H-isoindol-4-yl}-2-thiophenecarboxamide

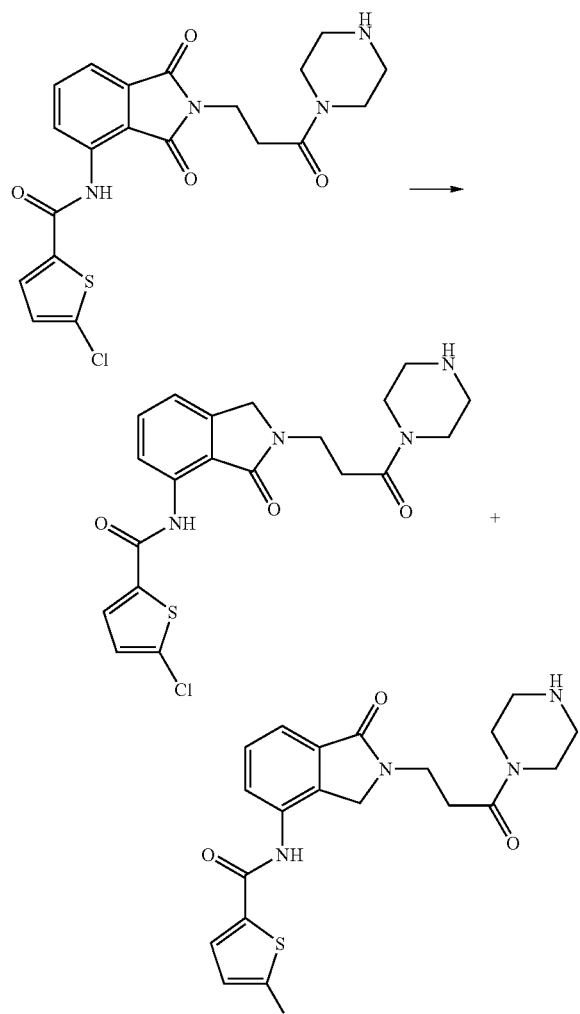

511 mg (1.14 mmol) of 5-chloro-N-{1,3-dioxo-2-[3-oxo-3-(1-piperazinyl)propyl]-2,3-dihydro-1H-isoindol-4-yl}-2-thiophenecarboxamide are suspended in 30 ml of methanol, and 216 mg (5.72 mmol) of sodium borohydride are added. The reaction mixture is stirred at room temperature for 4 h, then carefully acidified with 2 N hydrochloric acid, stirred for 20 min, made alkaline with 2 N aqueous sodium hydroxide solution and extracted three times with methylene chloride. The combined organic phases are dried over magnesium sulfate, filtered and concentrated.

The residue is dissolved in 20 ml of methylene chloride, and 1.07 g (9.36 mmol) of trifluoroacetic acid and 181 mg (1.56 mmol) of triethylsilane are added. The reaction mixture is stirred at room temperature overnight and then concentrated. The residue is chromatographed on silica gel (CH$_2$Cl$_2$/EtOH/conc. aqu. ammonia solution=20/1/0.01 to 5/1/0.01).

This gives 170 mg of the 3-oxo isomer (MS=433 (M+H), rt (Method 5)=2.86 min) and 168 mg of the 1-oxo isomer (MS=433 (M+H), rt (Method 5)=2.47 min).

Example 98

5-Chloro-N-{3-hydroxy-2-[2-(1-methyl-2-pyrrolidinyl)ethyl]-1-oxo-2,3-dihydro-1H-isoindol-4-yl}-2-thiophenecarboxamide and 5-chloro-N-{1-hydroxy-2-[2-(1-methyl-2-pyrrolidinyl)ethyl]-3-oxo-2,3-dihydro-1H-isoindol-4-yl}-2-thiophenecarboxamide

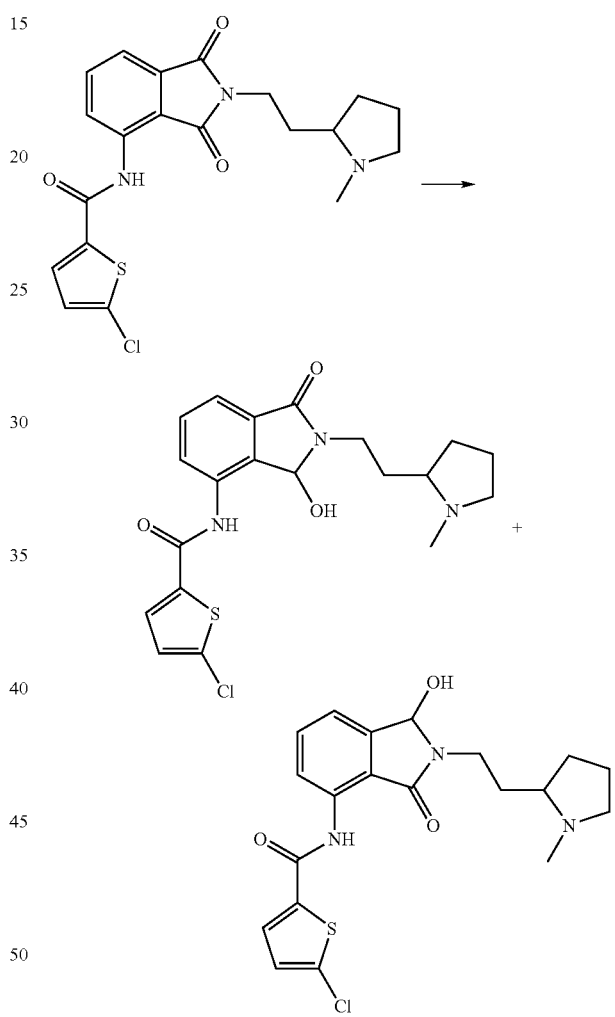

553 mg (1.32 mmol) of 5-chloro-N-{2-[2-(1-methyl-2-pyrrolidinyl)ethyl]-1,3-dioxo-2,3-dihydro-1H-isoindol-4-yl}-2-thiophenecarboxamide are dissolved in 20 ml of methanol, and 250 mg (6.62 mmol) of sodium borohydride are added. After 4 h of stirring at RT, the reaction mixture is carefully acidified with 2 N hydrochloric acid, stirred vigorously for 20 min, made alkaline using 2 N aqueous sodium hydroxide solution and extracted three times with dichloromethane. The combined organic phases are dried over MgSO$_4$, filtered and concentrated.

This gives 545 mg (97% of theory) of the product as a mixture of isomers.

MS=420 (M+H), LC (Method 6): rt=2.41 min and 2.75 min.

Example 99

5-Chloro-N-{2-[2-(1-methyl-2-pyrrolidinyl)ethyl]-1-oxo-2,3-dihydro-1H-isoindol-4-yl}-2-thiophenecarboxamide and 5-chloro-N-{2-[2-(1-methyl-2-pyrrolidinyl)ethyl]-3-oxo-2,3-dihydro-1H-isoindol-4-yl}-2-thiophenecarboxamide

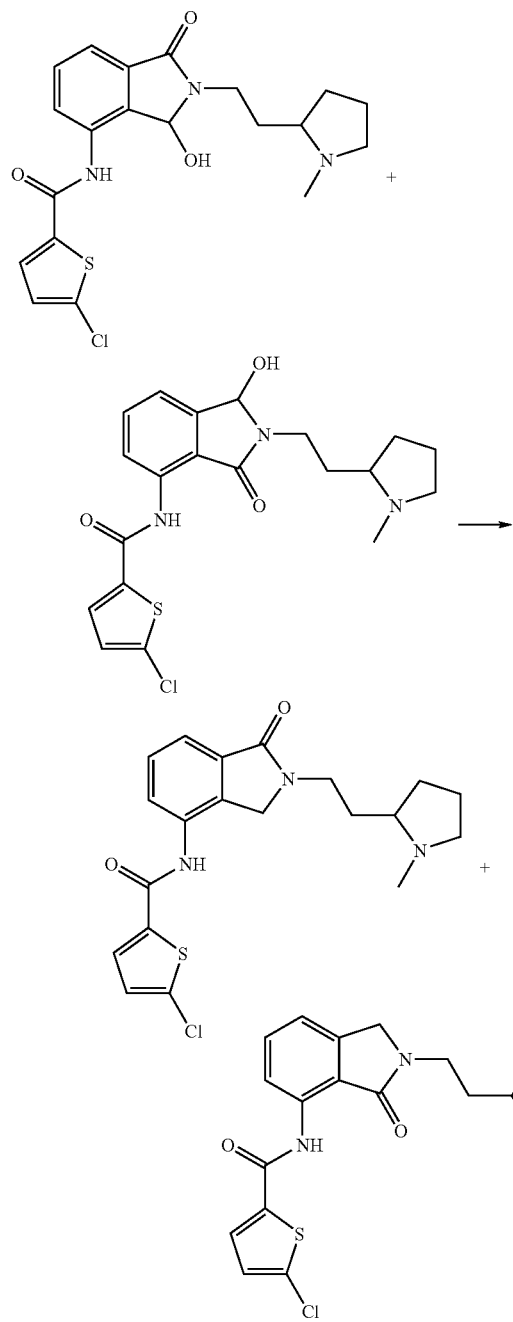

530 mg (1.26 mmol) of an isomer mixture of 5-chloro-N-{3-hydroxy-2-[2-(1-methyl-2-pyrrolidinyl)ethyl]-1-oxo-2,3-dihydro-1H-isoindol-4-yl}-2-thiophenecarboxamide and 5-chloro-N-{1-hydroxy-2-[2-(1-methyl-2-pyrrolidinyl)ethyl]-3-oxo-2,3-dihydro-1H-isoindol-4-yl}-2-thiophenecarboxamide are dissolved in 15 ml of dichloromethane. 17.27 g (15.15 mmol) of trifluoroacetic acid and 293.5 mg (2.52 mmol) of triethylsilane are added. The reaction mixture is stirred at RT overnight and then diluted with dichloromethane and washed with 2 N aqueous sodium hydroxide solution. The organic phase is dried over MgSO$_4$, filtered and concentrated. The crude product is chromatographed on silica gel (CH$_2$Cl$_2$/EtOH/conc. aqueous ammonia solution=50/1/0.01 to 20/1/0.01).

The 3-oxo isomer is eluted first. 196 mg (38% of theory) of this product are obtained; MS=404 (M+H), LC (Method 5): rt=2.90.

The yield of 1-oxo isomer is 248 mg (49% of theory); MS=404 (M+H), LC (Method 5): rt=2.49 min.

Example 100 tert-Butyl 4-[2-(4-{[(5-chloro-2-thienyl)carbonyl]amino}-1-methoxy-3-oxo-1,3-dihydro-2H-isoindol-2-yl)ethyl]-1-piperidinecarboxylate and tert-butyl 4-[2-(4-{[(5-chloro-2-thienyl)carbonyl]amino}-3-methoxy-1-oxo-1,3-dihydro-2H-isoindol-2-yl)ethyl]-1-piperidinecarboxylate

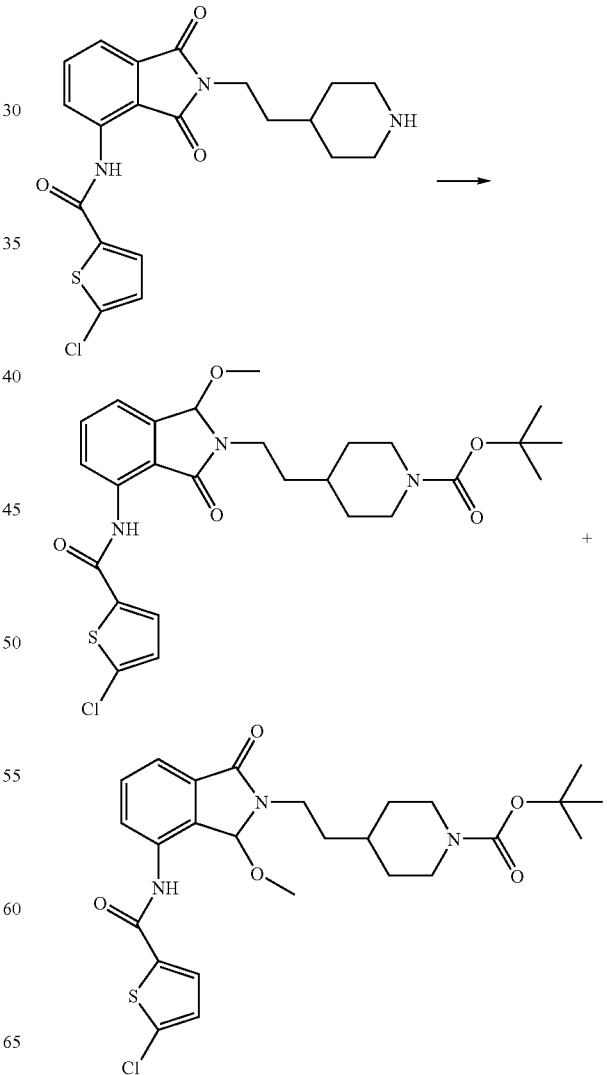

1.05 g (2.51 mmol) of 5-chloro-N-{1,3-dioxo-2-[2-(4-piperidinyl)ethyl]-2,3-dihydro-1H-isoindol-4-yl}-2-thiophenecarboxamide are dissolved in 15 ml of dichloromethane and 15 ml of methanol and cooled to 0° C., and 143 mg (3.77 mmol) of sodium borohydride are added a little at a time. The mixture is stirred at room temperature overnight and then acidified slightly with 1N hydrochloric acid solution and extracted with dichloromethane. The organic phase is dried over magnesium sulfate and concentrated. The aqueous phase is concentrated by evaporation. The two residues are combined, taken up in 15 ml of 1,4-dioxane and, at 0° C., 0.82 g (3.77 mmol) of di-tert-butyl dicarbonate and 15 ml of 1N sodium hydroxide solution are added. After 15 min, ice-cooling is removed, and the mixture is stirred at room temperature for a further 3.5 h and then, after dilution with water, extracted with dichloromethane. The organic extract is dried over magnesium sulfate and concentrated. The product mixture is separated by chromatography on silica gel (dichloromethane/methanol 98:2).

Yield: 400 mg (29.8% of theory) of the 1-methoxy-3-oxo isomer; LC-MS: m/z (%)=551 (M+NH$_4^+$, 30), 534 (M+H, 75), 434 (100); HPLC (Method 1): rt (%)=5.56 (100).

Yield: 560 mg (41.7% of theory) of the 3-methoxy-1-oxo isomer LC-MS: m/z (%)=551 (M+NH$_4^+$, 20), 502 (85), 402 (100); HPLC (Method 6): rt (%)=4.84 (79).

Example 101

5-Chloro-N-{3-oxo-2-[2-(4-piperidinyl)ethyl]-2,3-dihydro-1H-isoindol-4-yl}-2-thiophenecarboxamide

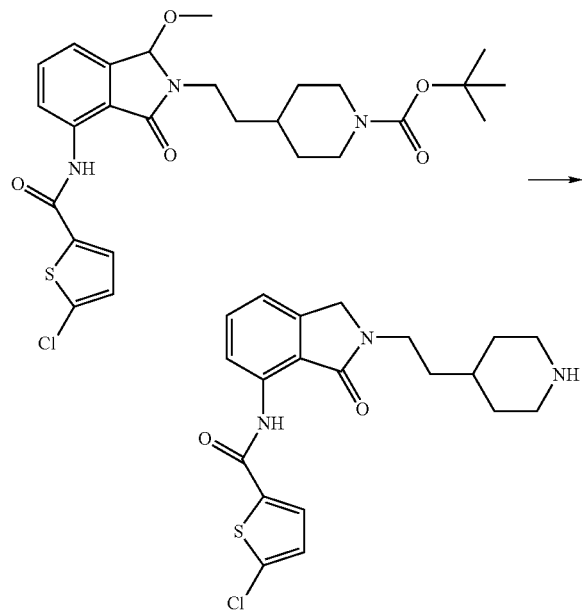

0.23 ml (1.4 mmol) of triethylsilane is added to a solution of 378 mg (0.704 mmol) of tert-butyl 4-[2-(4-{[(5-chloro-2-thienyl)carbonyl]amino}-1-methoxy-3-oxo-1,3-dihydro-2H-isoindol-2-yl)ethyl]-1-piperidinecarboxylate in 12 ml of dichloromethane and 0.65 ml of trifluoroacetic acid. The mixture is stirred overnight, concentrated and taken up in dichloromethane. The solution is washed with 1N sodium hydroxide solution, dried and concentrated. The residue is crystallized using diethyl ether. The resulting solid is purified further by chromatography on silica gel (gradient from dichloromethane/methanol 95:5 to dichloromethane/methanol/triethylamine 9:1:0.1).

Yield: 144 mg (50.5% of theory). MS (DCI, NH$_4$): m/z (%)=404 (M+H, 100); HPLC (Method 3): rt (%)=4.19 (91).

Example 102

In an analogous manner, 5-chloro-N-{1-oxo-2-[2-(4-piperidinyl)ethyl]-2,3-dihydro-1H-isoindol-4-yl}-2-thiophenecarboxamide can be prepared from tert-butyl 4-[2-(4-{[(5-chloro-2-thienyl)carbonyl]amino}-3-methoxy-1-oxo-1,3-dihydro-2H-isoindol-2-yl)ethyl]-1-piperidinecarboxylate.

MS (ESI): m/z (%)=404 (M+H, 86), 305 (100); HPLC (Method 2): rt (%)=3.93 (96).

Preparation of 5-chloro-N-{2-[2-hydroxy-3-(1-piperazinyl)propyl]-1,3-dioxo-2,3-dihydro-1H-isoindol-4-yl}-2-thiophenecarboxamide derivatives from 5-chloro-N-(1,3-dioxo-2,3-dihydro-1H-isoindol-4-yl)-2-thiophenecarboxamide

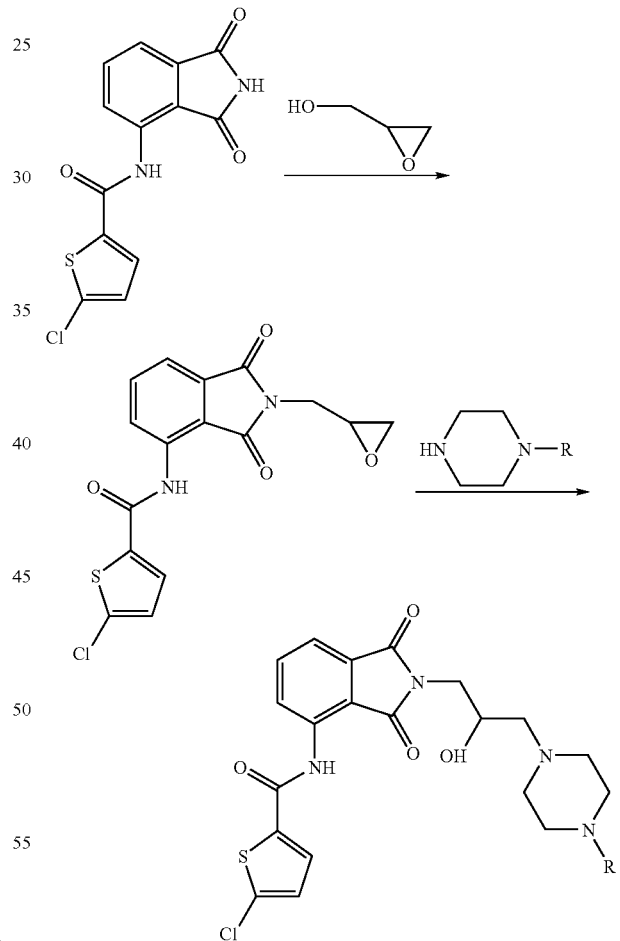

Example 103

5-Chloro-N-[2-(2-oxiranylmethyl)-1,3-dioxo-2,3-dihydro-1H-isoindol-4-yl]-2-thiophenecarboxaamide Under argon and at room temperature, diethyl azodicarboxylate (1.1 eq.) is added dropwise to a solution of 5-chloro-N-(1,3-dioxo-2,3-dihydro-1H-isoindol-4-yl)-2-thiophenecarboxamide, (R/S)-2,3-epoxy-1-propanol (1.1 eq.) and triphenylphosphine (1.1 eq.) in tetrahydrofuran (0.1 mol/l). The reaction mixture is stirred for 16–20 h, and water is added. After addition of dichloromethane and phase separation, the aqueous phase is extracted with dichloromethane and the combined organic phases are dried (sodium sulfate), filtered and concentrated under reduced pressure. The desired product is purified by flash chromatography (cyclohexane/ethyl acetate mixtures).

MS (DCI, $NH_3$): m/z (%)=380 ([M+$NH_4$]$^+$, 100), Cl pattern; HPLC (Method 1): rt=4.69 min.

Under argon and at room temperature, triethylamine (1 eq.) is added to a solution of the epoxide and the substituted piperazine (1.2 eq.) in tetrahydrofuran (0.1 mol/l). The reaction mixture is heated under reflux for 3 d and then concentrated under reduced pressure. The desired product is purified by flash chromatography (dichloromethane/methanol mixtures).

The following compounds were prepared analogously:

Example 104

5-Chloro-N-(2-{2-hydroxy-3-[4-(4-pyridinyl)-1-piperazinyl]propyl}-1,3-dioxo-2,3-dihydro-1H-isoindol-4-yl)-2-thiophenecarboxamide MS (ESI): m/z (%)=526 ([M+H]$^+$, 100), Cl pattern; HPLC (Method 1): rt=3.68 min.

Example 105

5-Chloro-N-(2-{2-hydroxy-3-[4-(2-methoxyphenyl)-1-piperazinyl]propyl}-1,3-dioxo-2,3-dihydro-1H-isoindol-4-yl)-2-thiophenecarboxamide MS (ESI): m/z (%)=555 ([M+H]$^+$, 100), Cl pattern; HPLC (Method 2): rt=3.97 min.

Example 106

5-Chloro-N-(2-{3-[4-(2-fluorophenyl)-1-piperazinyl]-2-hydroxypropyl}-1,3-dioxo-2,3-dihydro-1H-isoindol-4-yl)-2-thiophenecarboxamide MS (ESI): m/z (%)=543 ([M+H]$^+$, 100), Cl pattern; HPLC (Method 2): rt=4.00 min.

Example 107

5-Chloro-N-(2-{3-[4-(4-fluorophenyl)-1-piperazinyl]-2-hydroxypropyl}-1,3-dioxo-2,3-dihydro-1H-isoindol-4-yl)-2-thiophenecarboxamide MS (ESI): m/z (%)=543 ([M+H]$^+$, 100), Cl pattern; HPLC (Method 2): rt=4.01 min.

Example 108

5-Chloro-N-(2-{2-hydroxy-3-[4-(2-pyridinyl)-1-piperazinyl]propyl}-1,3-dioxo-2,3-dihydro-1H-isoindol-4-yl)-2-thiophenecarboxanmide MS (ESI): m/z (%)=526 ([M+H]$^+$, 100), Cl pattern; HPLC (Method 2): rt=3.36 min.

Example 109

5-Chloro-N-(2-{2-hydroxy-3-[4-(2-nitrophenyl)-1-piperazinyl]propyl}-1,3-dioxo-2,3-dihydro-1H-isoindol-4-yl)-2-thiophenecarboxamide MS (ESI): m/z (%)=570 ([M+H]$^+$, 100), Cl pattern; HPLC (Method 2): rt=4.00 min.

Example 110

5-Chloro-N-(2-{3-[4-(4-chlorophenyl)-1-piperazinyl]-2-hydroxypropyl}-1,3-dioxo-2,3-dihydro-1H-isoindol-4-yl)-2-thiophenecarboxamide MS (ESI): m/z (%)=559 ([M+H]$^+$, 100), $Cl_2$ pattern; HPLC (Method 2): rt=4.05 min.

Example 111

5-Chloro-N-(2-{2-hydroxy-3-[4-(3-methylphenyl)-1-piperazinyl]propyl}-1,3-dioxo-2,3-dihydro-1H-isoindol-4-yl)-2-thiophenecarboxamide MS (ESI): m/z (%)=539 ([M+H]$^+$, 100), Cl pattern; HPLC (Method 2): rt=3.97 min.

Example 112

5-Chloro-N-{2-[3-(4-cyclohexyl-1-piperazinyl)-2-hydroxypropyl]-1,3-dioxo-2,3-dihydro-1H-isoindol-4-yl}-2-thiophenecarboxamide MS (ESI): m/z (%)=531 ([M+H]$^+$, 100), Cl pattern; HPLC (Method 2): rt=3.53 min.

Example 113

5-Chloro-N-(2-{2-hydroxy-3-[4-(2-pyrimidinyl)-1-piperazinyl]propyl}-1,3-dioxo-2,3-dihydro-1H-isoindol-4-yl)-2-thiophenecarboxamide MS (ESI): m/z (%)=527 ([M+H]$^+$, 100), Cl pattern; HPLC (Method 2): rt=3.66 min.

Example 114

5-Chloro-N-(2-{3-[4-(2,4-difluorophenyl)-1-piperazinyl]-2-hydroxypropyl}-1,3-dioxo-2,3-dihydro-1H-isoindol-4-yl)-2-thiophenecarboxamide MS (ESI): m/z (%)=561 ([M+H]$^+$, 100), Cl pattern; HPLC (Method 2): rt=4.01 min.

Example 115

5-Chloro-N-{2-[2-hydroxy-3-(4-phenyl-1-piperazinyl)propyl]-1,3-dioxo-2,3-dihydro-1H-isoindol-4-yl}-2-thiophenecarboxamide MS (ESI): m/z (%)=525 ([M+H]$^+$, 100), Cl pattern; HPLC (Method 2): rt=3.92 min.

Example 116

5-Chloro-N-[2-(2-hydroxy-3-{4-[3-(trifluoromethyl)phenyl]-1-piperazinyl}-propyl)-1,3-dioxo-2,3-dihydro-1H-isoindol-4-yl]-2-thiophenecarboxamide MS (ESI): m/z (%)=593 ([M+H]$^+$, 100), Cl pattern; HPLC (Method 2): rt=4.33 min.

Example 117

5-Chloro-N-(2-{2-hydroxy-3-[4-(4-methoxyphenyl)-1-piperazinyl]propyl}-1,3-dioxo-2,3-dihydro-1H-isoindol-4-yl)-2-thiophenecarboxamide MS (ESI): m/z (%)=555 ([M+H]$^+$, 100), Cl pattern; HPLC (Method 2): rt=4.05 min.

Example 118

N-{2-[3-(1,4'-Bipiperidin-1'-yl)-2-hydroxypropyl]-1,3-dioxo-2,3-dihydro-1H-isoindol-4-yl}-5-chloro-2-thiophenecarboxamide MS (ESI): m/z (%)=531 ([M+H]$^+$, 100), Cl pattern; HPLC (Method 4): rt=2.56 min.

The two compounds below can be prepared by reducing the corresponding phthalimides using i) NaBH4, ii) TFA, Et$_3$SiH:

Example 119

5-Chloro-N-(2-{2-hydroxy-3-[4-(4-pyridinyl)-1-piperazinyl]propyl}-1-oxo-2,3-dihydro-1H-isoindol-4-yl)-2-thiophenecarboxamide MS (ESI): m/z (%)=512 ([M+H]$^+$, 100), Cl pattern; HPLC (Method 4): rt=2.16 min.

Example 120

5-Chloro-N-(2-{2-hydroxy-3-[4-(4-pyridinyl)-1-piperazinyl]propyl}-3-oxo-2,3-dihydro-1H-isoindol-4-yl)-2-thiophenecarboxamide MS (ESI): m/z (%)=512 ([M+H]$^+$, 100), Cl pattern; HPLC (Method 4): rt=2.50 min.

The invention claimed is:

1. A compound of the formula (I)

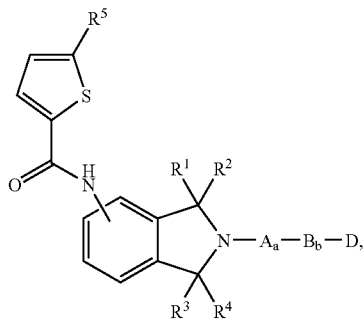

in which $R^1$ and $R^2$ together represent O and
$R^3$ and $R^4$ together represent O, or $R^1$ represents hydrogen, hydroxy or $(C_1$–$C_4)$-alkoxy,
$R^2$ represents hydrogen and
$R^3$ and $R^4$ together represent O, or $R^1$ and $R^2$ together represent O,
$R^3$ represents hydrogen, hydroxy or $(C_1$–$C_4)$-alkoxy and
$R^4$ represents hydrogen,
$R^5$ represents halogen, trifluoromethyl or methyl,
A represents $(C_1$–$C_4)$-alkanediyl which may be substituted by hydroxy or $(C_1$–$C_4)$-alkoxy,
a represents 0 or 1,
B represents a group

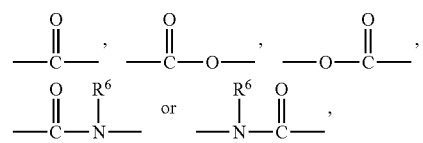

in which $R^6$ represents hydrogen or $(C_1$–$C_4)$-alkyl,
b represents 0 or 1,
D represents piperidinyl,
which may be mono- or disubstituted, independently of one another, by hydroxy, carbamoyl, $(C_1$–$C_4)$-alkanoyl, $(C_3$–$C_7)$-cycloalkanoyl, $(C_3$–$C_7)$-cycloalkyl, 5- to 10-membered heterocyclyl, $(C_1$–$C_4)$-alkoxycarbonyl, $(C_1$–$C_6)$-alkyl,
which for its part may be substituted by hydroxy, cyano, $(C_1$–$C_4)$-alkoxy, mono- or di-$(C_1$–$C_6)$-alkylamino, mono- or di-$(C_1$–$C_6)$-alkylaminocarbonyl, 5- to 10-membered heterocyclyl, 5- or 6-membered heterocyclylcarbonyl or 5- to 10-membered heteroaryl,
$(C_6$–$C_{10})$-aryl,
which for its part may be substituted by halogen, trifluoromethyl, nitro,
$(C_1$–$C_4)$-alkyl or $(C_1$–$C_4)$-alkoxy,
5- to 10-membered heteroaryl,
which for its part may be substituted by cyano, amino or $(C_1$–$C_4)$-alkyl,
or 5- to 10-membered heteroarylcarbonyl,
or a salt, hydrate, hydrate of the salt, or solvate thereof.

2. The compound as claimed in claim 1,
in which
the thiophenecarboxylic acid substituent is attached to the phenyl ring in the ortho-position to the point of attachment of the fused heterocycle,
$R^1$ and $R^2$ together represent O and
$R^3$ and $R^4$ together represent O, or $R^1$ represents hydrogen, hydroxy, methoxy or ethoxy,
$R^2$ represents hydrogen and
$R^3$ and $R^4$ together represent O, or $R^1$ and $R^2$ together represent O,
$R^3$ represents hydrogen, hydroxy, methoxy or ethoxy and
$R^4$ represents hydrogen,
$R^5$ represents halogen or trifluoromethyl,
A represents $(C_1$–$C_4)$-alkanediyl, which may be substituted by hydroxy,
a represents 0 or 1, B represents a group

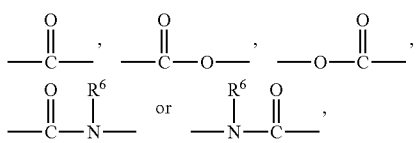

in which
R⁶ represents hydrogen,
b represents 0 or 1,
D represents piperidinyl,
which may be mono- or disubstituted, independently of one another, by hydroxy, carbamoyl, acetyl, cyclopropanoyl, ($C_3$–$C_6$)-cycloalkyl, 5- to 10-membered heterocyclyl, ($C_1$–$C_3$)-alkyl,
which for its part may be substituted by hydroxy, methoxy, mono- or dimethylamino, mono- or di-($C_1$–$C_3$)-alkylaminocarbonyl, 5- or 6-membered heterocyclyl, 5- or 6-membered heterocyclylcarbonyl or 5- or 6-membered heteroaryl,
phenyl,
which for its part may be substituted by fluorine, chlorine, trifluoromethyl, methyl or methoxy,
or 5- or 6-membered heteroaryl,
which for its part may be substituted by cyano, amino or methyl,
or a salt, hydrate, hydrate of the salt, or solvate thereof.

3. The compound as claimed in claim 1,
in which
the thiophenecarboxylic acid substituent is attached to the phenyl ring in the ortho-position to the point of attachment of the fused heterocycle,
$R^1$ and $R^2$ together represent O and
$R^3$ and $R^4$ together represent O,
or
$R^1$ represents hydrogen, hydroxy or methoxy
$R^2$ represents hydrogen and
$R^3$ and $R^4$ together represent O,
or
$R^1$ and $R^2$ together represent O,
$R^3$ represents hydrogen, hydroxy or methoxy and
$R^4$ represents hydrogen,
$R^5$ represents chlorine or bromine,
A represents methanediyl, ethanediyl or propane-1,3-diyl, which radicals may be substituted by hydroxy,
a represents 0 or 1,
B represents a group

b represents 0 or 1,
D represents piperidine,
which may be mono- or disubstituted, independently of one another,
by methyl, ethyl, n-propyl or isopropyl,
which for their part may be substituted by hydroxy or pyridyl,
or pyridyl,
which for its part may be substituted by amino or methyl,
or a salt, hydrate, hydrate of the salt, or solvate thereof.

4. A process for preparing compounds of the formula (1) as defined in claim 1, characterized in that
(B1) a compound of the formula (XI)

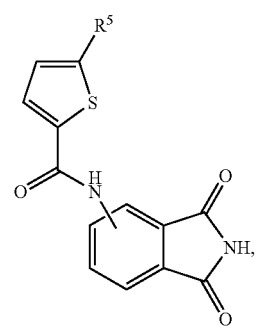

(XI)

in which $R^5$ is as defined in claim 1,
is converted with a compound of the formula (XII)

HO-A$_a$-B$_b$-D (XII), in which A, a, B, b and D are as defined in claim 1,
into compound of the formula (I),
where the resulting compound of the formula (I) may, if appropriate, subsequently be subjected to further derivatizations which can be carried out by customary methods.

5. A pharmaceutical composition, comprising at least one compound of the formula (I) as defined in claim 1 and at least one pharmaceutically acceptable carrier.

6. A method for the treatment of a thromboembolic disorders selected from the group consisting of myocardial infarction, angina pectoris, reocclusions and restenoses after angioplasty or aortocoronary bypass, stroke, transitory ischemic attacks, peripheral arterial occlusive diseases, pulmonary embolisms and deep venous thromboses, comprising administering an effective amount of a compound of claim 1.

7. The method of claim 6 wherein said angina pectoris is unstable angina.

* * * * *